United States Patent
Buck et al.

(10) Patent No.: US 9,498,129 B2
(45) Date of Patent: Nov. 22, 2016

(54) METHOD AND DEVICE FOR PATIENT MONITORING USING DYNAMIC MULTI-FUNCTION DEVICE

(71) Applicant: Cardiac Technologies International, Inc., Santa Fe, NM (US)

(72) Inventors: Ryan Buck, Santa Fe, NM (US); Frederick M. Hijazi, Santa Fe, NM (US)

(73) Assignee: Cardiac Technologies International, Inc., Santa Fe, NM (US)

( * ) Notice: Subject to any disclaimer, the term of this patent is extended or adjusted under 35 U.S.C. 154(b) by 0 days.

(21) Appl. No.: 14/660,515

(22) Filed: Mar. 17, 2015

(65) Prior Publication Data

US 2015/0257647 A1 Sep. 17, 2015

Related U.S. Application Data

(60) Provisional application No. 61/954,501, filed on Mar. 17, 2014.

(51) Int. Cl.
*A61B 5/00* (2006.01)
*A61B 5/0402* (2006.01)
*A61B 5/0408* (2006.01)
*A61B 5/0432* (2006.01)

(52) U.S. Cl.
CPC .......... *A61B 5/0028* (2013.01); *A61B 5/0006* (2013.01); *A61B 5/0402* (2013.01); *A61B 5/6833* (2013.01); *A61B 5/0432* (2013.01); *A61B 5/04085* (2013.01); *A61B 5/04087* (2013.01); *A61B 5/6804* (2013.01); *A61B 2560/0204* (2013.01)

(58) Field of Classification Search
None
See application file for complete search history.

(56) References Cited

U.S. PATENT DOCUMENTS

| | | | |
|---|---|---|---|
| 6,211,799 B1* | 4/2001 | Post | A61B 5/0028 340/10.51 |
| 8,224,244 B2* | 7/2012 | Kim | H04B 13/005 340/13.22 |
| 2007/0145945 A1* | 6/2007 | McGinley | H02J 7/00 320/114 |
| 2009/0063193 A1* | 3/2009 | Barton | A61N 1/37282 705/3 |
| 2012/0165633 A1* | 6/2012 | Khair | A61B 5/04028 600/345 |

* cited by examiner

*Primary Examiner* — Brian T Gedeon
(74) *Attorney, Agent, or Firm* — Sheridan Ross P.C.

(57) ABSTRACT

The present invention is directed to an improved method, system and product to provide wireless ECG patient monitoring. Although embodiments make specific reference to monitoring electrocardiogram signal with an adherent patch, the system methods, and device herein may be applicable to any application in which physiological monitoring is used. The present invention also presents a reliable means for docking the interface while minimizing signal interference and user error. In addition, a novel means for transmitting and receiving a patient's ECG measurements is introduced which includes the use of an epidermal communication network (ECN) and an ECG enabled module for ECN communications and interface. Although embodiments make specific reference to the use of the ECN for ECG measurements, the system methods, and protocol herein may be applicable to any wearable device and/or other smart device which is ECN enabled.

3 Claims, 11 Drawing Sheets

PRIOR ART

METHOD AND DEVICE FOR PATIENT MONITORING USING DYNAMIC MULTI-FUNCTION DEVICE

FIELD OF THE INVENTION

The present invention is directed to a method, system and device for simple wireless electrocardiogram monitoring. In particular, the invention is directed to the use of a wireless ECG with reliable functionality, data-log information access, intrinsically safe charging, and capacity to communicate via an epidermal communication network. Communication over the epidermal communication network can occur in conjunction with an epidermal communication network enabled module.

BACKGROUND

Heart disease is the leading cause of death in the United States. A heart attack, also known as an acute myocardial infarction (AMI), typically results from a blood clot or "thrombus" that obstructs blood flow in one or more coronary arteries. AMI is a common and life-threatening complication of coronary artery disease. Coronary ischemia is caused by an insufficiency of oxygen to the heart muscle. Ischemia is typically provoked by physical activity or other causes of increased heart rate when one or more of the coronary arteries is narrowed by atherosclerosis. AMI, which is typically the result of a completely blocked coronary artery, is the most extreme form of ischemia. Patients will often (but not always) become aware of chest discomfort, known as "angina", when the heart muscle is experiencing ischemia. Those with coronary atherosclerosis are at higher risk for AMI if the plaque becomes further obstructed by thrombus.

Detection of AMI often involves analyzing changes in a person's ST segment voltage. A common scheme for computing changes in the ST segment involves determining a quantity known as ST deviation for each beat. ST deviation is the value of the electrocardiogram at a point or points during the ST segment relative to the value of the electrocardiogram at some point or points during the PQ segment. Whether or not a particular ST deviation is indicative of AMI depends on a comparison of that ST deviation with a threshold.

Acute myocardial infarction and ischemia may be detected from a patient's electrocardiogram (ECG). An ECG is a highly useful diagnostic aid for clinicians, for the study of heart rate and rhythm. An electrocardiogram is defined to be the heart's electrical signal as sensed through skin surface electrodes that are placed in a position to indicate the heart's electrical activity. The ECG indicates the propagation of low amplitude electrical signals, commonly referred to as the cardiac impulse, across the myocardium giving information about depolarization and repolarization characteristics of the heart.

An ECG typically receives signals from a plurality of electrodes (3, 5, and 12 are common numbers). Historically, the 12-lead surface electrocardiograph has been the most commonly used. A surface ECG refers to placement of electrodes on the surface, or skin, of the patient as opposed to directly to cardiac tissue which obviously requires an invasive procedure. This method attaches about 10 wired electrodes to a patient's body in order to measure the bio-potential activity of the patient and uses the electrodes to transfer the information into the electrocardiogram. The measurement is possible because electric activity surfaces from the cardiac muscle to the skin and dissipates throughout the conductive skin layer. Since the skin has electric impedances, the conductivity of the electric current varies depending on the direction of the measurement and the separation distance of between the measurement electrodes. The ECG monitors voltage signals appearing between various pairs of the electrodes and performs a vector analysis of the resultant signal pairs to prepare various two-dimensional voltage-time graphs indicative of internal cardiac activity.

ECG measurements have been conducted for over 200 years, and a standard configuration of the measurement vector leads have been adopted by the medical and engineering communities. This standard of leads formation and configuration require substantial separation of points of measurements on the surface of the skin, which necessitates connection of two remote points by lead wires into an instrumentation amplifier. This large separation between electrode contact points maximizes the surface area of the skin between the measurement electrode points and therefore maximizes the impedance, and measured voltage potential across the contact electrodes.

The use of the conventional ECG requires large separation between electrodes in order maximize impedance and measure the voltage potential across the contact electrodes. The required separation, leads to large wired footprints on the patient.

If the distance d is too small the bipolar ECG signals will be buried in the noise. If d is increased the signals will increase and in the most extreme variant the measuring electrodes will be positioned as in the EASI system, stretching over the whole torso. However, in the EASI system four unipolar measurements are used to synthesize a standard 12-lead system. In the process of synthesizing ECG from non-standard electrode placement (such as the EASI system and the system disclosed herein) parameters are used to transform the non uniform ECG to standard ECG leads. However, the variance in body impedance between different people is an evident source of error.

Further, the use of a wired monitoring system makes taking a patient's ECG very uncomfortable. Even further, wired devices make patient monitoring very cumbersome for the practitioners and increases the probability of infection due to the exposure of bodily fluid by the wires. To overcome these shortcomings associated with wired monitoring, the use of wireless monitoring devices is being investigated. Wireless monitoring devices will provide increased comfort for a patient, decreased lead-off alarms due to tugged wires, reduced error in lead connection and reduced substantial motion artifacts and RF interference.

Further, providing an epidermal communication network (ECN) where these and other wireless devices can communicate without the need for wired or wireless connectivity can further enhance a user's experience, reduce power consumption and increase data throughput. The ECN is a novel communication means for transmitting and receiving information across the human body. By using the human body as a communication network, seamless integration of smaller, less obstructive, and more naturally integrated wireless sensors across the entire body can be possible.

In U.S. Pat. App. No. 2012/0165633 to Mohammad Khair, partial wireless monitoring was introduced. The ECG measurement system uses wired electrodes only for calibration purposes. In this method, the calibration is started from the ECG receiver unit which sends selection signals and synchronization pulses via its radio module to the radio module of each ECG sensing unit. As a consequence, preselected passive electrodes are connected to each ECG sensing unit, in predetermined sequences, such that the measuring module of each ECG sensing unit generates signals. Following an A/D-conversion and data processing in the data processing unit, local bipolar data for each ECG sensing unit and calculated standard ECG data are stored digitally in a buffer memory in the data processing unit. This digitally stored data representing one and the same heart beat, are then compared in order to determine the parameters of a transfer function by which the standard ECG leads may be synthesized from the local bipolar ECG data. Once these parameters have been determined, the calibration phase can be terminated and the passive electrodes can be detached from the body of the patient and the multi cable connection can be disconnected from the ECG sensing units.

However, this solution is not a complete wireless solution and the use of wired electrodes still makes it very cumbersome to work with. With the current advancements in technology and electronics (i.e. the use of instrumentation amplifiers), the separation required for ECG measurements is decreasing, thus making it easier to find a reliable wireless monitoring device.

In U.S. Pat. No. 5,811,897 to Spaude et al, a device for body-bound data transmission is introduced and incorporated herein in its entirety. The transmission of the data between two terminals in which a portion of the body of a user completes the data transmission circuit is described. A first terminal is worn by a body of a user, and an interface is provided for coupling the data signals into the body and/or for coupling them out of the body. A second terminal with a touch-sensitive interface by way of which, in the case of a contact by the body wearing the first terminal, couples data signals coupled into the body out of the body and/or couples data signals into the body.

However, this solution is not the most efficient. It requires the use of two or more pairs of electrodes on each part of the body terminals. Further, the solution presented by Spaude requires the transmission of signals through the body as high frequencies are referenced. A need for a wireless single electrode solution communicating at low frequencies with low power consumption is needed. Therefore, it is the object of the current embodiment to present a wireless monitoring device with the capability to communicate over an epidermal communication network.

SUMMARY OF THE INVENTION

The present invention is directed to an improved method, system and product to provide wireless ECG patient monitoring. Although embodiments make specific reference to monitoring electrocardiogram signals with an adherent patch, the system, methods, and device herein may be applicable to any application in which physiological monitoring is used. Unlike prior art methods and devices which require a wired solution to enable patient monitoring, this solution presents a safe, intuitive means for making ECG measurements without the use of wires. It is therefore an object of the present invention to provide a leadless wireless, ECG measurement system and method for measuring of bio-potential electrical activity, while having improved design and performance as compared to prior art systems. It is another object of the present invention to provide a leadless, wireless ECG measurement system and method for measuring of bio-potential electrical activity of the heart which uses measurements across smaller separation distances between the electrode contact points as compared to prior art systems. It is still another object of the present invention to provide an ECG measurement system and method which is much more compact in its form and coverage area as compared to prior art systems. It is still yet another object of the present invention to provide an ECG measurement system and method which produces a higher degree of comfort for the patient by eliminating lead wires extending to distal electrodes. It is another object of the present invention to present an ECG measurement system and method that is easier to use and provides greater flexibility in placement for the user, does not decrease measurement accuracy and has a smaller footprint than other conventional ECG devices. It is yet another object of the present invention to use an Epidermal Communication Network (ECN) to transmit ECG measurements a remote center. It is another object of the present invention to provide an epidermal communication network that permits synchronization between sensors and/or communication between individual sensors, network of sensors, ECN enabled sensors, ECN modules, and ECN enabled interfaces, etc. In still another embodiment of the present invention, the single electrode wearable sensors communicate on the epidermal layer of the body at very low frequencies.

These and other objects, features and advantages of the invention are provided by a leadless wireless ECG measurement system for measuring of bio-potential electrical activity of the heart in a patient's body which includes at least one multi-contact bio-potential electrode assembly adapted for attachment (or close orientation to) to the patient's body. In one embodiment, the electrode assembly is formed of an electronic patch layer and a disposable electrode layer. The disposable electrode layer can have a plurality of contact points for engagement with the surface of the patient's body and is configured to measure ECG signals in response to electrical activity in the heart. Furthermore, the present invention also presents a reliable means for docking the monitoring device to an interface while minimizing signal interference and user error.

Certain embodiments of the present invention also provide a means for charging the device in an intrinsically safe manner. Certain embodiments employ strong magnetic contacts to retain portions in proper placement, e.g. between the mediums to enable a secure fit.

Still other embodiments of the present invention provide a mechanism for data-log access information. With the use of smart detection hardware, various embodiments can employ a device that can incorporate intelligent switching, which may be dynamically re-configured to detect various user inputs.

Still yet other embodiments of the present invention provide a method for synchronizing sensors in order to obtain reliable data, with synchronization providing a dependable way for obtaining bi-potential measurements.

The electronic component in any of the devices described herein may include a processor having a memory with computer readable instructions to record signals from the first and second electrodes while the electronic device is attached to the patient. In a preferred embodiment, the processor may be configured to only convert signals from the electrodes to digital signals, filter those signals and then store the signals in memory.

Various embodiments are directed to the provision of a device and method for the monitoring of a patient, preferably in a manner such that detection, signaling, conveyance of signals and display of relevant information is accomplished with unprecedented speed, economically and with outside observers unaware that such a system is being employed. In many embodiments, the contacts may vary in size, shape and location. The particular dimensions, thickness, size, area surface, texture, flexibility, adhesive characteristics, and composition for the particular device can be adjusted as one of the skill in the art will appreciate.

In various embodiments of the present invention, the monitoring device is an adherent device that is adhered to a skin of the patient. In others, however, due to, for example, sensitivity to adhesives, especially over a prolonged period of time, other skin association mechanisms are employed to obtain desired contact. Thus, apparel can be fitted so that there are apertures that permit skin contact with electrodes so as to achieve solid contact needed for signal communications. While the discussion herein is primarily directed to adhesive patches, it will be understood that other electrode contact means are possible to employ and are well within the scope of the present invention. In many embodiments of the present invention, an electrocardiogram signal is measured when the adherent patch is adhered to the patient or docketed to an interface. An adhesive patch with an adhesive to adhere the support to the patient is preferably used. The adhesive patch may comprise a breathable tape with adhesive to adhere the support to the patient. The adhesive patch may further encompass a piece of soft material with an adhesive that can cover a part of the body as described in U.S. Pat. No. 8,460,189 entitled "Adherent Cardiac Monitor with Advanced Sensing Capabilities" issued to Libbus et al., on Jun. 11, 2013, which is further incorporated by reference herein.

The adhesive patch can aid in providing a better fit and conductivity in placement of the monitoring device for better adherence and increased signal quality in transmission over an epidermal communication network. The adhesive device can further include micro-spikes which aid in the coupling and signal transfer between the monitoring device and/or another wearable device, a wired device, a wireless device and other devices of the like. The microspikes can include an adhesive bandage, patch, or other similar material on the monitoring device or on as a separate mechanism that includes miniature speared objects that can minimally penetrate the skin to a more conductive layer for better user coupling and signal transmission. Alternatively or in addition, a body lotion or other viscous substance can be applied on the epidermis of the user to increase the conductivity for better signal transmission.

Another aspect of the present invention is directed to the use of an interface between a disposable multi-electrode patch and the enclosure. In one embodiment of the present invention, conductive magnetic contacts may be used for each of the signal inputs. In many embodiments, the number and arrangement of the contacts may vary and be arranged in a number of ways. Still yet in another embodiment, an annular configuration may be used with n-electrodes for better signal quality and to provide other properties such as but not limited to obtaining n-angles of the cardiac potential. By using magnetic contacts, the monitoring device achieves a stronger contact along the analog signal pathways. The interface presented also provides seamless integration between the electrode inputs and the analog front-end circuitry. By using a magnetic ring along both the perimeter of the multi-electrode patch and the bottom-side of the enclosure, secure coupling is achieved. In many embodiments, the disposable electrode side needs to be employed by magnets. In other embodiments, the coupling is achieved by using a material with a highly magnetic permeability such as, but not limited to an un-magnetized iron.

Another aspect of the present invention is directed to the use of four inputs arranged on the periphery of the top-side of the module. In many embodiments, the arrangement of the contacts may be arranged in any manner. The contacts may be arranged in a circular, triangular, rectangular or any other arrangement, and in several embodiments, preferably in a parallel manner. In another embodiment, the number of contacts may be any number greater than two. For example, n conductive elements may be arranged around the circumference of the device. In another embodiment, four contacts can be used for charging and the others for use in a capacitive touch interface. Further, the four inputs need not be magnetic.

In other embodiments, the wireless device may be positioned at various locations throughout the body including but not limited to the chest, shoulders, ribs, sides, back of shoulders and back. Securement to various portions of a person's body may be by way of clothing, bandages, adhesive patches, etc. In certain embodiments, apparel is adapted to specifically receive the device, such as inside a woman's bra—so that the device may be placed into contact with the person's skin while still being unnoticeable to outside observers.

In another embodiment, the contacts may be positioned on the bottom surface of the device with the electrodes electrically connected to the electronic component. The device may further be shaped in a circular, triangular, rectangular or other desired geometric configuration, preferably one that has a contacting contour that is comfortable and specially adapted to rest in a recess of a person's body so as not to be noticeable when clothing is worn by such person. The adhesive device may include wings which house the electrically connected electrodes. In another embodiment, the location of the electronic components may be modified such that all or substantially all of the electronic components are within a housing. Wings associated with the device/housing may be provided that are free from electronic components. In many embodiments, the wing is more flexible than the housing. In another embodiment, the wings and the housing are made from the same material. In other embodiments, however, the wings and the housing are made from different materials. Certain embodiments include wings made from a fabric, or a synthetic fiber. As one of skill in the art will appreciate, various materials and orientations will be appreciated in view of the guidance provided herein, including a more detailed description as described in U.S. Appl. No. 2011/0279962 entitled "Device Features and Design Elements for Long-Term Adhesion" published to Kumar et al, on Nov. 17, 2011, which is further incorporated by reference herein.

In one embodiment of the present invention, the contacts may be embedded into the enclosure such that they are flushed to the surface. In many embodiments, contact exposure may vary and may be recessed, exposed, entirely exposed, or not exposed.

In another aspect, embodiments of the present invention provide for a DC mode configuration for the plurality (e.g. four) of magnetic contacts. In some embodiments, configuration in an asymmetrical configuration insures proper alignment due to the magnetic polarities of the contacts. Further, by having a charging sleeve and a docking counterpart with identical asymmetric configuration, one possible fit is available providing a guide to the user in docking the interface and the module. In another embodiment, more than four contacts may be used. Four contacts may be used for charging and the rest may be used for other purposes such as a user interface.

In many embodiments, the DC mode configuration further provides a strong magnetic force which exerts a strong interaction between modules providing an intrinsically safe device. In many embodiments, the inputs need not be magnetic, and other methods for fastening the module may be employed, such methods of fastening including but not limited to implementing a male/female grove or notch type docking mechanism, screw or bayoneted closure features, etc.

In another embodiment of this invention, the DC mode configuration also provides a means for minimizing signal interference, such means well known to those of skill in the art and not listed herein. The static arrangement between the magnetic contacts within the enclosure ensures signal integrity by enabling a secure area such that the magnetic fields do not impact the signal.

In another embodiment, the magnets may be gold plated in order to ensure efficient charge transfer. Gold plating is a highly stable and conducting metal. Using gold also helps prevent corrosion caused by the exposure to various environmental conditions. However, other conductive metals may be used, such as silver and copper. Further, conduction may also be ensured through the use of spring-loaded contacts.

In another embodiment of this invention, the DC mode configuration also provides an enclosure free from environmental restrictions. The enclosure of the present invention may provide a means for restricting sweat, bio-fouling and other wet conditions know to one in the art from entering the module. Other embodiments of the present invention provide a method for charging the monitoring device used for monitoring the patient. Upon docking with the module, the contacts facilitate charge transfer.

In many embodiments, the plurality (e.g. four) of magnetic contacts are used for charging at least high energy-density batteries used in a communication system between a charger and the device. One possible arrangement may include a cathode, an anode, and the other two contacts may are assigned SMCLK and SMDATA roles from a system bus protocol. This permits the incorporation of a communication module between a charger and a module. Incorporating such a module enables the integration of a host processor and thus provide for additional data exchange between with the charger. The data exchange can include but is not limited to an indication alert. The alert can come from at least but not limited to an LED alert, a piezo or user interface. In another embodiment of the present invention, during the device charging the alert indicator may be come obscured during a critical event. In still other embodiments, the indicator can be an LCD screen or communication device.

In certain embodiments, the communication device used as an indicator can use other technologies to display the information regarding the ECG reading to the user. For example, some systems for displaying information may utilize "heads-up" displays. A heads-up display is typically positioned near the user's eyes to allow the user to view displayed images or information with little or no head movement. To generate the images on the display, a computer processing system may be used as described in U.S. Pat. No. 8,482,487 entitled "Displaying objects on separate eye displays" issued to Rhodes, et al., on Jul. 9, 2013, which is further incorporated by reference herein. In a preferred embodiment, the "heads-up" display may be used to display patient ECG readings. The monitoring device could communicate with a "heads-up" display such as Google Glasses to provide the user with additional information regarding the monitoring device. Such information may include vitals, user profile, and even a warning if a reading is outside the norm.

In one embodiment of the present invention, two contacts can used as measurement electrodes and the other two may be used for orientation purposes such as placement of an accelerometer, as described in U.S. Pat. No. 8,460,189 entitled "Adherent Cardiac Monitor with Advanced Sensing Capabilities" issued to Libbus et al, on Jun. 11, 2013, which is further incorporated by reference herein.

Further, the adherent device comprises an accelerometer and at least two measurement electrodes. The at least two measurement electrodes can be separated by a distance to define an electrode measurement axis. An accelerometer signal is measured when the device is adhered to the patient. An orientation of the electrode measurement axis on the patient is determined in response to the accelerometer signal. In a preferred embodiment of this invention, the electrodes may be concentrically organized around the perimeter of the path providing high-speed dynamic multiplexing. This variation would allow any pair of electrodes to be selected at any given time.

In another embodiment of the present invention, the monitoring system may be disposable. The wireless ECG unit is preferably implemented as an integrated adhesive disposable patch for applying to a subject's body and for obtaining and transferring local non-standard ECG data and standard ECG data to a receiver unit. Alternatively, the ECG sensing unit 100 may be implemented as reusable unit with snap connections to available disposable electrodes. As described in U.S. Pat. No. 8,315,695 entitled "System and method for wireless generation of standard ECG leads and an ECG sensing unit therefore" issued to Sebelius et al, on Nov. 12, 2012, which is further incorporated by reference herein.

In many embodiments of the present invention, the patient monitoring system may be reusable with disposable parts, reusable, or completely disposable.

In another aspect of the present invention, the monitoring device may be configured to include a user interface. The magnetic contact configuration can be used by doctors in order to retrieve a patient's information by means of a scroll wheel. The magnetic contacts preferably serve as a multi-input capacitive touch user-interface and even more preferably the magnetic contacts are positioned at various locations as the wheel is adjusted, providing for varying services including but not limited to patient's records, ECG data and other menu items.

In one embodiment of the present invention, the multi-user interface functions and works as a locking mechanism. The use of the scroll wheel provides a safe means for locking the device which avoids accidental triggers. The scroll wheel works similar to that of a pattern-lock on a smartphone. That is to say, the wheel has to be rotated in a series of directions (i.e. 2 turns clockwise, 1 counterclockwise) to enable patient input. In many embodiments of the present invention, the number of contacts vary, increasing the number of patterns that may be added. In one embodiment, the user input screen may be configured to time-out after non-used for a predetermined number of minutes.

In another embodiment, the capacitive touch device maybe directed to the use of the interactive scheme in which the monitoring device may be wirelessly controlled by a peripheral communication device. Such communication device may include but not limited to a laptop, tablet, smartphone, etc. Such external connectivity provides further control and customization the device. The user may now have access to dynamic switching, zooming and programming (i.e. entering user data, network info, selecting menu options, etc.)

In another embodiment, the adherent device may continuously monitor physiological parameters, communicate wirelessly with a remote center, and provide alerts when necessary. The system may comprise an adherent patch, which attaches to the patient's body and contains sensing electrodes, battery, memory, logic, and wireless communication capabilities. In some embodiments, the patch can communicate with the remote center, via the intermediate device in the patient's home. In some embodiments, remote center receives the patient data and applies a patient evaluation algorithm, for example an algorithm to calculate the apnea hypopnea index. When a flag is raised, the center may communicate with the patient, hospital, nurse, and/or physician to allow for therapeutic intervention as described in U.S. Pat. No. 8,460,189 entitled "Adherent Cardiac Monitor with Advanced Sensing Capabilities" issued to Libbus et al, on Jun. 11, 2013, which is further incorporated by reference herein.

The adherent device can wirelessly communicate with a remote center. The communication may occur directly (via a cellular or Wi-Fi network), or indirectly through an intermediate device. An intermediate device may consist of multiple devices, which can communicate wired or wirelessly to relay data to a remote center.

In another embodiment, the adherent device can communicate with a remote center via an Epidermal Communication Network (ECN). The epidermal communication network is a novel communication network, method, and protocol that enables data from the adherent device, external device, interface module, etc., to be transmitted across the epidermal layer of the body. Because electrons can travel across a medium when a potential difference in energy or voltage is present, and the human body is capable of holding potential differences across its frame, the epidermal layer of the body can be used to carry electrical signals. The physical properties of the epidermal layer provide a medium which allows electrical signals to directly interface and/or be applied to the epidermal layer of the human body, which is well suited to carry signals along the exterior surface. By treating the human body as a conductor, the body acts as a physical wire connecting one or more devices and allows data to be transmitted and received by the devices. Therefore, if an electrical signal is directly applied to the human body, it is possible to read/measure the potential difference at a point in the body. Further, data can be digitized onto the human body and stored until needed, allowing the body to act like a storage medium, much like, but not limited to, a flash drive, hard drive, RAM, ROM, DRAM, SDRAM, and other storage devices and media.

In one embodiment, the signal can travel through the body and a signal handling device can be used. As appreciated in view of the guidance provided herein, including a more detailed description as described in U.S. Pub. No. 2014/0348270 entitled "Handling of Signals Transmitted Through a Human Body" to Badu et al. on Nov. 27, 2014, which is further incorporated by reference herein, various combinations of signal transmission and wearable devices are within the scope of the present invention.

In many embodiments, the capacitive touch user interface can be configured to take ECG measurements. In another embodiment, the interface provides the user with a confirmation and verification of the signal integrity used in the ECG measurement. In emergency situations where signal integrity is critical, doctors need to have access to signals with minimal affects due to noise or distortion. To accomplish this, the signal inputs are routed through an analog multiplexer to the analog to digital converter inputs. These inputs are by nature very high impedance (just as primary electrodes on the reverse side of the device) and thus may be considered passive such that there is no danger presented to the patient. Such dangers include but are not limited to short-circuit potential. To confirm signal integrity, a Lead I measurement is taken. A standard Lead I is a differential measurement that is comprised of the voltage measurement at the left arm with respect to the voltage measured at the right arm. In using the interface, this measurement is accomplished by placing a finger from the left hand is placed onto the designated contact for Left-Arm, and two fingers from the right hand are placed onto a designated contacts for Right-Arm and Right-Leg Drive. This results in Lead I ECG waveform. In another embodiment, a standard Lead II may be measured by taking the voltage differential at the right arm with respect to the voltage measured at the left leg. Still in another embodiment, a standard Lead III may be measured by taking the voltage differential at the left arm with respect to the voltage measured at the left leg. In many embodiments, the number of contacts needed for signal verification could vary in number with a minimum of one contact required. Simple heart rate detection may be accomplished with one magnetic contact.

In one embodiment, an electrical conductive strap or garment system is used to allow communication between wearable electronics. The electric conductive garment can be a strap, a tie, a fastener, a strip, clasp, a clip, a pin, a button, a zipper, a belt, and any other securing mechanism that can be used. The conductive strap can be used to power electronic devices. In one embodiment, the communication between the wearable sensors can be entirely through conductive threads, fabrics, etc. linking the sensors through the wearable garment. In other embodiments, the conductive strap can further work in conjunction with other communication mediums such as wired, wireless, and ECN communications. As one of skill in the art will appreciate, various applications, methods, and systems for communicating between wearable devices is possible. As appreciated in view of the guidance provided herein, including a more detailed description as described in U.S. Pat. No. 6,350,129 entitled "Wearable Electronics Conductive Garments Strap and System" issued to Gorlick et al. on Feb. 6, 2002, which is further incorporated by reference herein, various combinations of the wearable devices are within the scope of the present invention.

In another embodiment of this invention, the monitoring device with capacitive touch user interface may also be equipped with smart detection hardware. The hardware is able to recognize various interactions with the device and adjust accordingly. For example, if the device is being worn in a noisy environment, the device may auto-correct itself to accommodate by adjusting its capacitive input baseline and threshold parameters. In many embodiments, the smart detection hardware may be configured to intelligently switch to allow for charging. In another embodiment, a required check is necessary to verify that the charger and the host are ready for charging, thus eliminating accidental discharge or a short circuit. In another embodiment, the charging pathway is physically disconnected from the external output (unless the above referenced check has been detected, in such case, charging may commence.

In many embodiments, the capacitive touch interface may be dispensed and replaced with a touch-based OLED display.

In another aspect of the present invention, the use of a human body as a signal transmission path can be incorporated such that the system includes a transmitter and a receiver. The signal can be carried through a path extending though the human body when a user carrying a transmitter touches the electrodes of the receiver. Various embodiments are possible, as will be appreciated in view of the guidance provided herein, including a more detailed description in U.S. Pat. No. 6,864,780 entitled "Data Transmission System using a Human Body as a Signal Transmission Path" issued to Doi on Mar. 8, 2005 and U.S. Pat. No. 6,771,161 entitled "Data Transmission System Using a Human Body as a Signal Transmission Path," issued to Doi et al, on Aug. 3, 2004, which are further incorporated by reference herein. In other embodiments, the receiver is not integrated into the external devices. Instead, a system on a module is proposed such that external devices can be incorporated and can still communicate with its own system. In still other embodiments, the use of biosensors can be used in conjunction with the data transmission system. Also, third party biosensor systems can work with the use of an interface in order to provide communication on the body using the data transmission system.

In still another aspect of the present invention, the use of the body for signal communication is presented without the use of an earth ground. Instead, the ECN can transmit and receive signals by conditioning an AC signal and coupling the signal on the epidermis of the body. Conditioning the signal can include modulation and amplification in order to increase the drive capacity of the signal in light of the resistive and capacitive load of the epidermis. Resonant networks that can be used include, but are not limited to LC resonant (both series and parallel), ceramic resonators, crystals, IC resonators and the combination thereof.

In another aspect of the present invention, device charging can occur by means of an inductive mechanism. In many embodiments, a charging coil may be integrated into the exterior of the device enclosure. The embedded coils used in this inductive charging scheme are wound concentrically around the sleeve of the enclosure. In another embodiment, the coils may be located outside the sleeve on the outer perimeter of the top surface, or anywhere on the device surface or in any arrangement on the sides of the module. In another embodiment of the invention, inductive charging is available while the four contact mediums are still present. In this configuration the inductive coils perform the charging, while the four contacts are utilized to ensure firm attachment between the device enclosure and the charging sleeve. The four contacts do not participate in charging the monitoring device in this configuration. Still in another embodiment, the contacts could also participate in the charging. In inductive charging, the outputs from the sleeve pass through the transmitter coil. The charging current which is coupled onto the receiving coil where it is rectified and conditioned to charge the smaller capacity on-board battery. In another embodiment, a modulator is applied such that the information may be transmitted between the charging unit and the device.

By implementing the inductive charging scheme with the integrated coil, the need for attachment of an external power source is eliminated. Instead, this scheme permits the user to recharge the device while in use. Further, because the battery is on the sleeve of the enclosure, it maybe recharged using standard DC-charging methods. To ensure that the device side is fully charge, a higher-capacity lithium-polymer battery on the charger side is preferred.

In another aspect of the invention, the device is batteryless. Through the process of energy harvesting, the wearable device is powered from external sources. In general, energy harvesting is the process by which energy from various sources such as, but not limited to, solar energy, thermal energy, wind energy, and kinetic energy, is collected and used to power the wearable device. Rectennas as well as nantennas can be implemented in the device for ambient harvesting as well.

In other embodiments of the invention, the human body can be used as a proximity sensor. Upon user input and once proximity is established, data transfer can take place by a wireless medium. Proximity sensing permits communication with another device for the purpose of reducing the energy consumption, thus, enabling the possible use of a batteryless device. In one embodiment, the human body communication system includes a controlled device measuring a capacitance that corresponds to the distance to human body, i.e. proximity sensing, which can then use the human body as a medium for transmitting a control command through the body. A wireless medium then transmits the actual data as described in U.S. App. No. 2007/0190940 entitled "System and Method for Human Body Communication" published to Lee et al, on Aug. 16, 2007, which is further incorporated by reference herein. Additionally, the method used in proximity sensing can include controlling the transmit power as described in U.S. Pat. No. 8,457,571 entitled "Apparatus and Method for Controlling Transmit Power in Human Body Communication System" to Kim et al, on Jun. 4, 2013, which is incorporated by reference herein. Further, the communication apparatus used for data communications using the human body as the transmission channel described in U.S. Pat. No. 8,224,244 entitled "Communication Apparatus" to Kim et. al, on Jul. 17, 2012 is incorporated by reference herein.

In other embodiments, an intelligent communication scheme is employed wherein human input is not required and proximity sensing and/or communication is dictated by the microcontroller itself. Communication occurs seamlessly without user input required.

In still another embodiment, there is no need to measure signal power or reliance on body proximity. Instead, the human body is used as the communication medium, as the information is transmitted on the epidermal layer of the body.

In yet another embodiment, the device can be ECN enabled. An ECN enabled device is a device with the ability to communicate via the epidermal communication network. By having a device which can communicate using an ECN, a drastic reduction in power consumption is observed as it pertains to inter-device communication on a human body. Thus, the energy savings can provide for a device that uses less power and is batteryless. As such, an ECN enabled device also has the capacity to use energy harvesting techniques to power up and function properly.

In other embodiments, the device is ECN enabled through the use of an ECN interface. An ECN interface, is an interface that permits users to interact with other smart devices via the ECN. By docking a device (such as the remote center) on an ECN interface, communication on the ECN is enabled, permitting transmission and reception of data to and from the wearable device via the human network. This communication can result in tremendous power savings, and may enable the use of devices powered using energy harvesting methods.

In other embodiments, an entire "smart device" is created on a module that also provides for access to communication on the ECN. The internal operation can be abstracted such that only the data I/O and control pins are exposed and an ECN interface is designed to fit the module. Such module/interface device can also, much like with the other ECN enabled devices described above, provide large power savings as compared to other communication alternatives such as, but not limited to, Bluetooth, BLE, ZigBee, Wi-Fi, WLAN, etc.

In one aspect of the invention, the monitoring device is used in monitoring applications where the sensors are located at various locations around the body. The various configurations account for varying differential voltage inputs. In one embodiment, the monitors may be used to monitor two independent heart beats. For example, the wireless electrocardiogram of a mother may be referenced and used in conjunction with a fetus to monitor fetal cardiac activity.

In one embodiment, a plurality of sensors can be used in body-coupled communications. In another embodiment, the plurality of sensors can transmit signals in conjunction with personal area networks (PAN) and/or Near-Field Intra-Body Communications. Communication signals transmitting on PAN or NFC work at RF frequencies. Still in another embodiment, a plurality of body coupled communication signals which have been detected via a plurality of electrodes can be used to generate a diversity output signal as described in U.S. Pat. No. 8,633,809 to Schenk et al., entitled "Electrode Diversity for Body-Coupled Communication Systems, on Jan. 21, 2014, which is further incorporated by reference herein.

In another embodiment, the body-coupled communication system can include only one electrode and thus uses only one transmission path for data transfer. In yet another embodiment, the body-coupled communication system works at very low frequencies requiring less signal processing and providing many-fold power savings.

In making ECG measurements, timing is of paramount importance; even a few milliseconds in delay may lead to a severely distorted reading. In ECG applications, exact timing is essential. Of primary concern is the fact that the human heart operates on a time scale that is much slower than the operating F of digital circuits. Therefore, in order to obtain accurate readings, even though electrodes are spaced apart, the measurements must be made simultaneously. To accomplish this, the electrodes are connected to an analog-to-digital converter, which uses a common clock and reference potential. The measurement taken is then a bipotential measurement.

In another aspect of the present invention, the monitoring device used at various locations in the body is synchronized to a reference to enable accurate measurements. In one embodiment of the present invention, a synchronized frame may be used in conjunction with the ADC and common clock to make the bipotential measurement. In one embodiment of the present invention, a crystal oscillator can be used for synchronization. The crystal oscillator generates the clocking signal. In another embodiment of the present invention, the RC oscillators may be used since they are less costly and consume less energy. Yet still in another embodiment of the present invention, a wireless synchronization frame is used. In many embodiments, wireless synchronization frames may be used with oscillators to correct time lag between sensors.

In one embodiment, complete wireless synchronization between units is presented. Synchronization between two separately located sensors is possible through the use of master-slave model. In this embodiment, one of the sensors plays the role of the master and one or more sensors act like slaves, synchronizing to the master. In one embodiment, a slave sensor may contain substantially less hardware than the master. In other embodiments, the slave may be much smaller in size than the master. The master sensor can combine, filter and analyze data collected and relayed from the slave sensors. The input data gathered by the slave sensors is transmitted wirelessly to the master sensor.

In a preferred embodiment, a unified synchronous clocking system between a master-slave network is presented. In this scheme, the clock signal is coupled to the patient allowing all the sensors to synchronize directly to this signal. The master device generates a stable low-frequency AC signal lying outside the frequency bandwidth of interest for measurement and drives this current into the patient's body via an output electrode. This output might also double as the right-leg drive output. The current output to the patient is of low enough frequency and magnitude to be completely benign to the patient (e.g. similar to transmission line coupling, or the RLD). This signal is thus accessible to all of the sensors in the network and servers as a unified reference clock input amongst devices. In order to generate the high clock rates needed for data-capture, processing, and wireless transmission (wireless transmission may require its own dedicated clock for practical purposes), the reference clock is used as the input to a phase locked loop multiplier onboard each sensor to generate high frequency clock signals within each device. Once each slave on the network is synchronized to the master-issued clock signal coupled onto the patient, frequency drift between devices is eliminated. By eliminating the frequency drift, the measurements are made simultaneously so that in the standard Lead I measurement, the RA and the LA measurements are preserved. Measurements of the signals of interest are unaffected by the presence of this signal as it will appear as a common-mode signal on differential input amplifiers or alternatively may be removed via a low pass filter. Further synchronization of data-sampling events may be enabled through modulations of the master-output clock signal which may serve as interrupts to cue data acquisition.

In order to obtain a potential measurement using this unified synchronous clocking network scheme, data from the analog-to-digital converters is loaded to the registers of a processor. The processor may be a microcontroller. This is possible by configuring the inputs as single ended inputs such that the measurement are made relative to identical high reference voltage on each device. The master device may then produce bipotential measurements across pairs of sensors by polling each device in the slave network. In many embodiments, at periodic intervals, reference frames may be inserted into the data in order to facilitate the combination of the single-ended inputs at the master prior to streaming wirelessly.

Still another aspect of the present embodiment, involves the use of an ECN network to obtain the ECG potential measurements. Potential measurements can be obtained by use of the epidermal communication network, wherein transmission and reception of data between devices using ECN facilitate measurements with more accuracy and simplified synchronization. In general, the communication between the wearable device and the smart device, internal device, ECN interface, etc. (i.e. remote center) entails the following. First, the raw data is sent, modified and/or a combination of both onto the epidermis via a slave/master. Next, the modified/raw data is received via the epidermis by the master/slave. Finally, if the data was modified, the inverse function is applied to yield the original raw data (i.e. the potential measurements). The simplest scenario is the direct input and/or output of the raw binary data onto the epidermal layer. In another scenario, the data requires at least one of encoding, modulation, conditioning, encryption and other signal processing.

In some instances, such as in ECG, Full 12-Lead ECG, and/or EEG potential measurements, conditioning, measurements and digitizing does not occur until the raw data arrives at the output, or other location of the body. The raw physiological signals are amplified, modulated/demodulated and sent without digitizing. By using an operational amplifier, the raw signal is amplified against a stable common reference, which affords a simple low cost solution without the use a microcontroller. The amplified signal is used as a gating/base input on a transistor with emitter/source pull to ground. Concurrently, an oscillator supplies the drain/collector input to the transistor, which leads to a modulated signal at the oscillator's frequency. This method permits the assignment of a unique carrier frequency to the inputs which allows differential measurements to be made as the signal is located by the "master" sensor located elsewhere in the epidermis.

An exemplary embodiment of this protocol implementation includes presetting the Master to a "ping frequency." The Master listens for the ping frequency on a predefined time interval on a reoccurring basis. A newly powered slave transmits this ping frequency which the Master then receives. Upon reception, the Master assigns a new "address frequency" to the slave, who in turn stores it in memory. The slave and Master communicate, (i.e. the system is now ECN enabled), as the Master recognizes the address frequency and the slave receives its own frequency. The direct amplification allows for wireless/leadless measurement of data from different locations on the body to be taken simultaneously and continuously without interfering with each other. Once the different signals (i.e. LA, RA, LL, etc.) are detected by the Master, the signals can be demodulated and fed to the remote center, or other device for generating the Lead data.

In another embodiment, synchronization on the epidermal communication network can occur via synchronous and/or asynchronous communication methods. Synchronous transmission entails synchronization by an external clock, while asynchronous transmission synchronizes by signals along the transmission medium. As previously stated, transmission on the ECN provides simplified synchronization over other embodiments. Because there is no clock signal accompanying the data on the epidermis, asynchronous methods can easily be adapted for ECN. In general, data-rates and arbitration can be processed prior to data transmission allowing one node to occupy the bus at a given time. In some embodiments, more than one node can occupy the bus at a given time. A predetermined arbitration scheme (protocol) can be employed to facilitate communication between a network of sensors on the epidermal bus. Time-division multiplexing, Frequency Division Multiplexing, Code Division Multiplexing, and/or Space Division Multiplexing can also be used. Additional system communications techniques are also possible, such as but not limited to, full-duplex communication and simultaneous asynchronous communication.

Synchronous communication, such as but not limited to, I2C, SPI, SDIO, etc. can also be implemented on the ECN. For synchronous communication, frequency mixing techniques can be employed, wherein specific frequency signatures would be assigned to the individual channels. Furthermore, both serial and parallel communication protocols can be adapted for communication on the ECN.

In another aspect of the present invention, the medical practitioner, nurse, technical assistant, cardiologist, etc., can use an ECN enabled sensor to obtain immediate access to a patient's vitals, records, and other medical and/or personal information. The user retrieving the information can obtain a patient's differential measurements through touch of the patient. That is, a patient's ECN is used to transfer the information from the ECG Lead sensors onto an ECN enabled sensor worn by the clinician.

In some embodiments, the clinician can use a wearable mounted display such as smart glasses to gather the information via the ECN. In this embodiment, the clinician and/or doctor can use smart glasses that are ENC enabled, to project information from and about the patient onto the screen of the eyeglass. Transmission between the patient and eyeglass can occur by patient touch through the ECN, wireless transmission, a wired transmission, and/or a combination thereof.

In another embodiment, the ECN enabled sensor from above can be a smart watch. The smart watch with for example, an LCD screen can be used to read a patients information. The smart watch can project the information read through the ECN onto the LCD screen. The smart watch can also be used to sense and monitor other relevant factors of a person and in conjunction with one or more other wearable devices for transmitting/receiving information. The epidermal communication network can work in conjunction with multiple smart devices. As an example, the smart watch can be used for taking a person's vitals such as temperature, hydration levels, blood pressure, sugar level, etc. Alternatively, the watch can be used in conjunction with other devices such as a ring or other piece of jewelry to monitor a person's oxygen level like in pulse oximetry. The finger is already known as an excellent location for SP02 measurements, thus, 2 LEDs can be incorporated on one side of the ring for the purposes of measuring blood oxygenation. The data is sent via an ECN to a master device such as or in conjunction with the watch or other device for further processing, display, or wireless communication. In other instances, watch and earring or other device can be used for hearing tests and/or hearing aids.

In one embodiment, the monitoring device or sensor can include a unique patient ID and telemetry system. The monitoring device includes ID circuitry that includes ID storage, a communication system which reads and transmits the unique ID from the ID storage, a power source and a pathway system to route the signals through the circuitry described in U.S. patent application Ser. No. 13/923,543 entitled "System Using Patient Monitoring Devices with Unique Patient ID's and Telemetry System" published to James Proud on Oct. 24, 2013 which is further incorporated by reference herein. In another embodiment, the monitoring device is ECN enabled and communicates via the epidermal communication network.

In another embodiment, the ECN network can work for and with one or more smart devices that are not the smart watch such as, but not limited to, a ring, a necklace, earrings, a money clip, a hair piece, buttons on a shirt, nose/eye/tongue ring, etc. Further, the ring for example, can be used not only for monitoring a patient's vitals, but can be used as a replacement or in conjunction with a wireless or wired mouse and/or combination thereof. In yet another embodiment, the ring can use motion, spatial and/or the combination thereof tracking by way of sensors such as but not limited to acoustic, electric/magnetic, location, pressure, thermal, and other smart sensing.

In one embodiment, the ring can act as a temperature monitoring device as described in U.S. Pat. No. 8,663,106 entitled "Non-Invasive Temperature Monitoring Device" published to Stivoric et al., on Mar. 4, 2014, which is further incorporated by reference herein. In another embodiment, the temperature monitoring device is ECN enabled and communicates via the epidermal communication network.

In other embodiments, the wearable sensors can be attached to a child's diapers. The sensor on the diaper can be used for monitoring a wet child, recording vital signs and even detecting more serious conditions such as S.I.D.S. The sensor can work in conjunction with the ECN network, a wireless network, a wired network, and/or a combination thereof.

The use of the ECN with other smart devices can include ECN enabled devices, wearable devices/sensors, wired devices, wireless devices, devices with ECN enabled interface, etc. Devices with an ECN Enabled Interface can include any device that works in conjunction with an attachment, software or combination thereof that allows the device to interact with ECN enabled wearables. The attachment, software, etc. is the interface that is incorporated into the existing device to allow the interaction on the epidermal communication network.

In another aspect of this invention, the ECN can be used as a means for transporting and/or facilitating the movement of information/data between various smart devices. For example, the ECN can be used to upload/download personal information onto a wearable device and/or external device. The wearable device can include, but is not limited to, a smartwatch, wrist-band, adhesive patch, garment, rings, smart glasses, necklace, etc. The external device can include a computer, laptop, smart phone, projector, scanners, and other such devices which may or may not include encryption which are or are not ECN enabled or interfaced.

Personal information and identification (i.e. credit card information, demographic information, login credentials, digital signatures, medical history and conditions, etc.) can be uploaded directly onto the wearable device via user interaction with the ECN enabled interface and stored on the wearable device memory. The information can be retrieved and downloaded at any time through touch with or interaction with other ECN enabled or interfaced devices. For example, a user may upload and store credit card information on an ECN enabled wearable (such as a wrist band) with an associated ECN Enabled Interface payment device tag, store the information, and later touch the payment interface at a venue, such as but not limited to a retail shop, airport, sporting arena, mall, coffee shop, etc., for access to the credit card information and other contents associated with the tag. Thus, a user is purchasing items and accessing his/her payment information by way of touch through the ECN network, which can replace and/or work in conjunction with RFIDs, QR codes, NFC communications, etc.

In many embodiments, information such as social security numbers, passwords, bank information, etc., requiring encryption and/or other security measures can be downloaded by requiring for example, a fingerprint scan in addition to the venue ECN enabled/interface device. In addition, encryption can be added to retrieve the secure information. Encryption can be enabled and the information retrieved by providing an encryption key assigned to a master sensor, which only the master sensor can retrieve. As an example, 128 AES encryption can be utilized. In still another embodiment, the fingerprint, encryption key and special ping frequency may be required to retrieve the secure information. Further, a fingerprint scan, multiple fingerprint scan, eyeball scan, and/or a combination thereof can be used alone or in conjunction with the above mentioned security measures.

In other embodiments, the user information can be encoded and used to unlock or enable consumer electronics. For example, a personal identification can be stored and used to open a garage door, enable the A/C, lock/unlock a door, unlock a smart phone, pair with an ECN enabled printer, automatically connect to a network access point, route directions from/to a navigation system, email accounts, Google accounts, etc.

In another embodiment, the ECN can be used for file transfer between devices. Files can include, but are not limited to pictures, videos, data structures, word documents, picture art, html files, XML files, etc. For example, a file containing user data on a health/fitness machine can be stored on a wearable device and accessed using the ECN. In another embodiment reading from the wearable device can be directed to health/fitness logs, measurements, monitoring, etc. The health/fitness/heart rate logs can occur using at least a photoplethysmographic sensor. The use of the photplethysmographic sensor can be include a periodic light source, a photo detector and other modules and/or components as described in U.S. Pat. No. 8,956,303 entitled "Wearable Heart Rate Monitor" issued to Hong et al. on Feb. 17, 2015, which is incorporated by reference herein.

In another example, a phone with an ECN enabled interface could upload data onto a small memory chip residing on a sensor and/or patch. Data is encoded over the ECN and stored until the user interacts with the intended device. Therefore, driving directions can be downloaded from a smart phone to an automobile navigation system with the use of the ECN patch and/or through an ECN enabled interface. Thus, the data file with directions is transferred from smart device to another without the need for Bluetooth or Wi-Fi connectivity.

In one aspect of the present invention, the ECN can work in conjunction with ingestible sensors for monitoring bio-electrochemical processes. By encapsulating an IC, testing and detection of malignant matter in a user can be detected. For example, the ingestible sensor can be used for detection of pathogens, cancers, toxins, antibodies, viruses, etc. Alternatively, the ingestible sensor can be used to test for chemical reactions to medications and treatments and even system responsiveness or in connection with ECG measurements. The ingestible sensor can work in conjunction with an epidermal communication network through near-field coupling, as a stand-alone, or with other wired or wireless systems, devices, networks and protocols.

In one embodiment, the ingestible sensor is swallowed and configured to receive stimulus inside the gastrointestinal tract of the user as described in U.S. patent application Ser. No. 11/851,221 entitled "Ingestible Low Power Sensor Device and System for Communicating with the Same" published to Amerson et al., on Jun. 19, 2008, which is further incorporated by reference herein.

In aspect of the present invention, the monitoring device is used to provide apparatus which will continuously monitor and analyze EKG or ECG signals generated by an ambulatory patient, diagnose abnormal events and instruct the patient on the manner of treatment required. In one embodiment, the present invention is to provide a portable computerized EKG monitor for performing real-time analysis of EKG signals to recognize and diagnose myocardial ischemic conditions and thereupon to immediately issue instructions for treatment or other action to the ambulatory user himself. In many embodiments, the device monitor can be a portable, lightweight computer which performs continuous real-time analysis of EKG information to detect, and alert an ambulatory user of, ischemic conditions, including the silent or pre-symptomatic type as described in U.S. Pat. No. 4,679,144 entitled "Cardiac signal real time monitor and method of analysis" issued to Cox et al. on Jul. 7, 1984, which is further incorporated by reference herein. In a preferred embodiment, the monitoring device is designed is wireless enabling the ambulatory personnel easier manipulation without the cumbersome use of wires while riding at high speeds. Still in another embodiment, the device monitor provides a means for wireless charging. The device may be configured to include a DC-mode or inductive mode charging such that in an emergency, power is not an issue.

In another aspect of the present invention, the device monitor may be configured for extended use. In many embodiments, the monitor is configured for patient comfort, such that the device can be worn and tolerated for extended periods of time. In one embodiment, a self-contained, wearable, portable ECG monitor is attached to the patient as described in U.S. Pat. No. 8,150,502 entitled "Non-Invasive Cardiac Monitor and Methods of Using Continuously Recorded Cardiac Data" published to Kumar et al, on Apr. 3, 2012, which is further incorporated by reference herein. The watertight chamber comprises separate watertight enclosures around each electrode of the at least two electrodes. A port for electronically accessing the electronic memory and a seal is provided on the port. The seal may be formed by the housing. In another embodiment, there is provided an activation or event notation button or switch formed in the housing that is accessible while the adhesive is affixed to the mammal. In one embodiment, actuation of an activation or event notation button or switch increases the fidelity of the ECG information stored in the electronic memory. In another embodiment, an indication of activation or event notation button or switch activation is stored in the electronic memory with contemporaneous ECG information. In yet another embodiment, there is provided an indicator that activates when ECG of the mammal is being detected. In another aspect, an indicator is provided that provides a continuous indication as long as ECG of the mammal is detected. In another embodiment, an indicator is provided that activates when a monitoring period is completed. In another embodiment, at least a portion of the housing is colored to match the skin tone of the mammal, or contain a decoration, art work, design, illustration or cartoon character to provide a custom appearance to the device. In a preferred embodiment, the watertight chamber includes a scroll wheel which enables the user to access the patient's information, ECG readings and other information acquired regarding the patient's vitals.

In another aspect of the present invention, a wireless heart rate monitor like device may be used to monitor a patient's cardiac state. The conventional heart rate monitor device consists of a chest strap sensor-transmitter and a wristwatch-type receiver. The chest strap sensor is worn around the chest during exercise. It has two electrodes, which are in constant contact with the skin, to detect electrical activities coming from the heart. Once the chest strap sensor-transmitter has picked up the heart signals, the information is wirelessly and continuously transmitted to the wristwatch. The number of heart beats per minute is then calculated and the value displayed on the wristwatch. Strapless heart rate monitors are typically wristwatch-type devices that may be preferred by users engaged in physical training because of convenience and combined time keeping features. In some cases the user is required to press a conductive contact on the face of the device to activate a pulse measurement sequence based on electrical sensing at the finger tip. However, this may require the user to interrupt physical activity, and does not always provide an "in-process" measurement and, therefore, may not be an accurate determination of heart rate during continuous exertion.

There are 2 sub-types of strapless heart rate monitors. The first type measures heart rate by detecting electrical impulses. Some wristwatch-type devices have electrodes on the device's underside in direct contact with the skin. These monitors are accurate (often called ECG or EKG accurate) but may be more costly. The second type of monitor measures heart rate by using optical sensors to detect pulses going through small blood vessels near the skin. These monitors based on optical sensors are less accurate than ECG type monitors but may be relatively less expensive. In a preferred embodiment, the wrist watch-time device may also communicate with another external device to provide a patient's vitals and may self-charge with the use of a DC-mode configuration.

In another aspect of the present invention, the monitoring device may be attached to a person's garment. The device connects to the garment by attaching or integrating one or more of the sensors into the garment, as described in U.S. Pat. Appl. No. 2012/0165645 entitled "System Method and Device for Monitoring Physiological Parameters of a Person" published to Russell et al. on Jun. 28, 2012, which is further incorporated by reference herein. The monitoring device comprises a bottom portion and a top portion that mate together to house an internal portion that comprises a processor, electronics, one or more transceivers, one or more light emitting LEDs. The bottom portion may include leaf springs (or other sensor pads) that conduct data from a plurality of sensors in or attached to the garment to the electronics (e.g., an ADC, DSP, or processor) of the internal portion. In another embodiment of this invention, the mobile device may include an OLED to alert in case of irregular potential reading. Still in another embodiment, the garment sensor may include an LCD screen in order to facilitate device interaction with other mobile devices.

In another aspect of the present invention, the monitoring device may be attached to a person's earphone. The device connects wirelessly or by wires to the ear of a human as described in U.S. App. No. 2014/0243617 entitled "Wearable Apparatus for Multiple Types of Physiological and/or Environmental Monitoring" published to LeBoeuf et al., on Aug. 28, 2014 and U.S. App. No. 2014/0243620 entitled "Physiological Monitoring Methods" published to LeBoeuf et al., on Aug. 28, 2014, which are further incorporated herein by this reference. A method for monitoring a subject via an earbud module includes positioning the earbud module within the ear of the person such that a sensor region matingly engages a region of the ear at the intersection of the anti tragus and acoustic meatus and is oriented in a direction away from the ear canal. Further, the wearable apparatus can be used for monitoring various physiological and environmental factors. Real-time, non-invasive health and environmental monitors include a plurality of compact sensors integrated within small, low-profile devices. In another embodiment, the earbud modules can work outside the ear, as part of an earring, attached to both or one ear, etc. In one embodiment, the earbud module can work in conjunction with other wearable devices or sensors for monitoring. Still in another embodiment, the earbud monitor can communicate wirelessly, through a wired medium, and/or the ECN.

It may be appreciated that many applications of the present invention may be formulated. One skilled in the art may appreciate that a network may include any system for exchanging data or transacting business, such as the Internet, an intranet, an extranet, DSL, WAN, LAN, Ethernet, satellite communications, and/or the like. It is noted that the network may be implemented as other types of networks, such as an interactive television (ITV) network.

A system user may interact with the system via any input device such as, a keypad, keyboard, mouse, kiosk, smart phone, e-reader, tablet, laptop, Ultrabook™, personal digital assistant, handheld computer (e.g., Palm Pilot®, Blackberry®, iPhone®, iPad®, Android®), cellular phone and/or the like. Similarly, the invention may be used in conjunction with any type of personal computer, network computer, work station, minicomputer, mainframe, smart phone, tablet, or the like running any operating system such as any version of Windows, MacOS, iOS, OS/2, BeOS, Linux, UNIX, Solaris, MVS, tablet operating system, smart phone operating system, or the like, including any future operating system or similar system. Moreover, although the invention may frequently be described as being implemented with TCP/IP communications protocol, it should be understood that the invention could also be implemented using SNA, IPX, Appletalk, IPte, NetBIOS, OSI or any number of communications protocols. Moreover, the system contemplates the use, sale, or distribution of any goods, services or information over any network having similar functionality described herein.

By way of providing additional background, context, and to further satisfy the written description requirements of 35 U.S.C. §112, the following references are incorporated by reference in their entireties for the express purpose of explaining the nature of ECGs, wireless sensors and other devices and to further describe the various apparatuses commonly associated therewith:

U.S. App. No. 2008/0177198 to Jang et al, discloses an apparatus to measure skin moisture content, that apparatus including: an electrode unit comprising a reference electrode, a current electrode, and a measuring electrode; an optional amplifier having an inverted input terminal connected with the R electrode.

U.S. Pat. App. No. 2012/0165633 to Khair, discloses a leadless wireless ECG measurement system for measuring of bio-potential electrical activity of the heart in a patient's body includes at least one multi-contact bio-potential electrode assembly adapted for attachment to the patient's body. The electrode assembly is formed of an electronic patch layer and a disposable electrode layer. The disposable electrode layer has a plurality of contact points for engagement with the surface of the patient's body and is configured to measure short-lead ECG signals in response to electrical activity in the heart. A processing unit is provided and is configured to produce a transfer function which computes estimated long-lead ECG signals based on the measured short-lead ECG signals from the plurality of contact points.

In U.S. Pat. No. 6,441,747 to Khair et al., on Aug. 27, 2002 and U.S. Pat. No. 6,496,705 to Ng et al., on Dec. 17, 2002, there are disclosed a wireless, programmable system for bio-potential signal acquisition which includes a base unit and a plurality of individual wireless, remotely programmable transceivers connected to patch electrodes. The base unit manages the transceivers by issuing registration, configuration, data acquisition, and transmission commands using wireless techniques. The bio-potential signals from the wireless transceivers are demultiplexed and supplied via a standard interface to a conventional ECG monitor for display.

U.S. Pat. No. 8,315,695 to Sebelius et al. on Nov. 12, 2012 and U.S. Pat. App. No. 2010/0234746 to Frederick Sebelius, disclose a system for wireless generation of at least one standard ECG lead comprises a plurality of electrodes for application to a subject at separate points thereof and a remote receiver station for generating at least one standard ECG lead from signals detected by a first group of said plurality of electrodes. The system further comprises a wireless sensing unit for generating at least two non-standard ECG signals from bipolar signals detected by a second group of the plurality of electrodes, a processor in the remote receiver station for calculation of a transform synthesizing each generated standard ECG lead from at least two of the non-standard ECG signals, a disconnection unit for disconnection of the first group of electrodes from the subject following the calculation, and a transfer unit for wireless transferring of the non-standard ECG signals to the remote receiver station following the disconnection of the first group of electrodes.

U.S. Pat. No. 7,403,808 to Istvan et al. on Jul. 22, 2008, discloses a cardiac monitoring system for detecting electrical signals from a patient's heart and wirelessly transmit the signals digitally to a remote base station via telemetry. The base station converts the digital signals to analog signals which can be read by an ECG monitor.

In U.S. Pat. No. 5,862,803 to Besson et al. on Jan. 26, 1999, U.S. Pat. No. 5,957,854 issued to Besson et al. on Sep. 28, 1999 and U.S. Pat. No. 6,289,238, also issued to Besson et al. on Sep. 11, 2001, discloses a wireless medical diagnosis and monitoring equipment which includes an evaluation station and a plurality of electrodes which are arranged on a patient. Each of the plurality of electrodes includes elementary sensors, sensor control, transceivers, and transmission control units which are integrated in one single semiconductor chip. The antenna that is arranged in this connection in the flexible electrode covering or directly in the chip.

In U.S. Pat. No. 4,981,141 to Jacob Segalowitz, on Jan. 1, 1991, there is disclosed an electrocardiographic monitoring system in which the heart-signal sensing electrodes are each coupled to the heart-signal monitor/recorder by respective wireless transmitters and corresponding respective receiving wireless receivers in a base unit.

U.S. Pat. No. 5,168,874 issued to Jacob Segalowitz, on Dec. 8, 1992, discloses a wireless electrode structure for use in patient monitoring system. It is a two-sectioned system having a plurality of micro-chipped, self-contained and self-powered heart signal sensing, amplifying, encoding and R-F transmitting, detecting electrodes and a receiving, demodulation and decoding base unit capable of developing real-time, signal averaging electrocardiography for a 12-lead ECG.

U.S. Pat. No. 5,307,818 issued to Jacob Segalowitz, discloses a precordial strip assembly medical monitoring system for use on a patient having skin, right and left arms and legs and a heart with a precordium lying thereover comprising an elongated strip having first and second surfaces.

U.S. App. No. 2014/0243694 to Baker et al, published Aug. 29, 2014 discloses a body-worn patient monitoring device which provides a substrate that supports one or more electrical connections to a patient's body. The method further includes determining a print pattern and thickness of a first material having a first resistivity to be printed on the substrate, determining a print pattern and thickness of a second material having a second resistivity to be printed on substrate, printing the second material onto the substrate wherein at least part of the second material overlays the first material.

U.S. App. No. 2014/0236249 to Rao et al., published Aug. 21, 2014 discloses a novel wearable electronic skin patch sensor device configured for the real time acquisition, processing and communicating cardiac activity and other types of biological information within a wired or wireless network. A system level scheme for networking the sensor device with client devices that include intelligent personal health management appliances, cellular telephones, PDAs, portable computers, RFID tags and servers is disclosed.

U.S. Pat. No. 5,796,827 to Coppersmith et al., published Aug. 18, 1998 discloses a system and method for near-field human coupling for encrypted communication with identification cards. The apparatus and method for encoding and transferring data from a transmitter to a receiver, using the human body as a transmission medium is disclosed.

U.S. Pat. No. 3,943,918, issued to Ronald A. Lewis, on Mar. 6, 1976 discloses disposable physiological telemetric device which includes a one-time use self-powering battery means, adhesive means, adhesive means for attachment of the device to the patient and electrodes for sensing the physiological functioning. A disposable cover is removed to expose the adhesive means and the battery means are actuated to power the device at the time of use. The radio frequency transmitter signal is received on suitable radio telemetry for monitoring and recording as desired.

U.S. Pat. No. 6,132,371 issued to Dempsey, et al., on Oct. 17, 2000 discloses a leadless monitoring of physiological conditions. The monitoring includes a transducer and a transponder. The transducer is adapted to sense the physiological condition of the patient and produce an output signal indicative of the sensed condition. The transponder is arranged to receive an electromagnetic signal and re-radiate the electromagnetic signal.

U.S. Pat. No. 4,679,144 issued to Cox, et al., on Jul. 7, 1987 discloses an apparatus for monitoring EKG information includes a programmable apparatus carried by an ambulatory patient for performing continuous, real-time analyses of EKG information derived from the patient. The apparatus facilitates the determination of the existence of various conditions based on these analyses which portend cardiac complications including myocardial ischemia, and arrhythemia activity and further instructs the patient on the manner of treatment required for the detected condition.

U.S. Pat. No. 8,430,310 issued to Ho, et al., on Apr. 30, 2013, discloses a system, method and device for identifying a user associated with a wearable electronic device. First, a directed electromagnetic radiation comprising an identifier associated with a user of the wearable electronic device is transmitted to a first target device. In response, a challenge signal is received requesting a verification response verifying the authenticity of the identifier. The wearable electronic device than detects a predefined user input, and responsive to receiving the challenge signal and detecting the predefined user input, transmits a challenge response corresponding to the predefined user input to a second target device. The first and second target devices may be the same device. The predefined user input may be comprise one or more sensed head movements and/or detected user input operations.

U.S. Pat. No. 8,482,487 issued to Rhodes, et al. on Jul. 9, 2013, discloses a method and device for displaying images. In some example embodiments, methods may include receiving data corresponding to an image. The image data may include at least one image object. Each image object may be assigned to either a foreground image set or a background image set. An embodiment may also include rendering a first display image based on at least the foreground image set. The first display image may include the objects assigned to the foreground image set. Additionally, the objects assigned to the foreground image set may be in focus in the first display image. Embodiments may also include rendering a second display image based on at least the background image set. The second display image may include the objects assigned to the background image set. Additionally, the objects assigned to the background image set may be in focus in the second display image.

U.S. Pat. Appl. No. 2014/0018635 to Buchheim et al. discloses a signal processing apparatus for determining a heart rate includes a plurality of sensors configured to detect changes in blood properties in a user's skin and a heart rate Kalman filter configured to compute a heart rate on the basis of signals obtained from the plurality of sensors. A method of computing a heart rate using the apparatus includes detecting changes in blood properties with a plurality of sensors, and computing with a heart rate Kalman filter the heart rate on the basis of signals obtained from the plurality of sensors.

The monitoring device may be configured to include a means for interacting with the user. The interaction can include a vibration; a intermittent or periodic beacon signal broadcast to an external device, flashing light emission, projection to an external device though text, email or other communication application. The interaction could also be via user interface. Such user interface may stem from the capacitive touch user interface in DC-mode configuration, in which the user interface may include an LCD screen or OLED.

The monitoring device may communicate via a wired media such as a wired network or direct-wired connection, and a wireless media such as acoustic, RF, IR or other wireless media. A wired link may include, for example, a parallel bus or a serial bus such as a Universal Serial Bus (USB). The communication device may communicate with a remote device via a connection. The connection may be wired and/or a wireless link. A wireless link may include, for example, Bluetooth, IEEE 802.11, Wi-Fi direct Cellular (such as GSM, CDMA, UMTS, EV-DO, WiMAX, or LTE or GPS), or ZigBee, among other possibilities. The connection between the monitoring device may function to transmit data and/or commands to and/or from the display device for transmission and/or reception by transmission/reception devices and/or may function to transmit display data for display on a display device such as but not limited to a projector, tablet, mobile device, smartphone, personal data assistant, a personal computer, a laptop computer, Google glasses, wrist watch-type device, or even docking the monitoring device on a communication device to download information or other computing device. The connection may comprise one or more base stations, routers, switches, LANs, WLANs, WANs, access points, or other network infrastructures. For example, the monitoring device may communicate with a cellular phone sending a text message regarding an abnormal cardiac reading it received.

For secure transmission of a patient's information to a communication device via a wireless link, the link may be secured via any one of a plurality of available wireless security protocols, including but not limited to, the Temporal Key Integrity Protocol (TKIP), the Extensible Authentication Protocol (EAP), the Lightweight Extensible Authentication Protocol (LEAP), the Protected Extensible Authentication Protocol (PEAP), WiFi Protected Access (WPA), the Advanced Encryption Standard (AES), and WLAN Authentication and Privacy Infrastructure (WAPI).

The monitoring device may be a single device or two or more components locking securely to provide accurate readings. Docking the various components securely may occur using any of a plurality of locking mechanisms, including but not limited to, Velcro, screws, solder, sealants, fasteners, welding which may include ultrasonic welding and magnets. For example, the monitoring device may use asymmetrical magnetic contacts for firm attachment.

The device may be configured in various ways including but not limited to circular, triangular, square, with wings, without wings. The contacts may be any magnetic metals such gold, silver, copper, iron or nickel. At least a portion of the enclosure may be colored to match the skin tone of the patient, or contain a decoration, art work, design, illustration or cartoon character to provide a custom appearance to the device. It may be transparent or at least partially translucent.

The wireless device may be positioned at various locations throughout the body including but not limited to the chest, shoulders, ribs, sides, back of shoulders and back. It can also be externally attached to a belt, a wallet, in a pant pocket. The monitoring device may be connected to a garment by attaching or integrating one or more of the sensors into the garment. Furthermore, the device may be made from at least one of, but not limited to metal, silicone, liquid silicone rubber, silicone elastomers, metals, hard plastics, flexible polymers, glass, polymethyl methacrylate (PMMA).

To comply with appropriate written description and enablement requirements and to provide sufficient guidance in how one of skill in the art can make and use the various embodiments of the present invention, incorporated herein in their entireties are the following: US Pat. Application Nos. 2014/0022163 to Olsson; and 2014/0066798 to Albert.

One or ordinary skill in the art will appreciate that embodiments of the present invention may be constructed of materials known to provide, or predictably manufactured to provide the various aspects of the present invention.

This Summary of the Invention is neither intended nor should it be construed as being representative of the full extent and scope of the present invention. The present invention is set forth in various levels of detail in the Summary of the Invention as well as in the attached drawings and the Detailed Description, and no limitation as to the scope of the present invention is intended by either the inclusion or non-inclusion of elements, components, etc. in this Summary of the Invention. Additional aspects of the present invention will become more readily apparent from the Detailed Description, particularly when taken together with the drawings.

The preceding is a simplified summary of the disclosure to provide an understanding of some aspects of the disclosure. This summary is neither an extensive nor exhaustive overview of the disclosure and its various aspects, embodiments, and/or configurations. It is intended neither to identify key or critical elements of the disclosure nor to delineate the scope of the disclosure but to present selected concepts of the disclosure in a simplified form as an introduction to the more detailed description presented below. One of skill in the art will appreciate that the entire disclosure, as well as the incorporated references, pictures, etcetera will provide a basis for the scope of the present invention as it may be claimed now and in future applications.

BRIEF DESCRIPTION OF THE DRAWINGS

The accompanying drawings, which are incorporated in and constitute a part of the specification, illustrate embodiments of the invention and together with the general description of the disclosure given above and the Detailed Description of the drawings given below, serve to explain the principles of the disclosures. The present disclosure is described in conjunction with the appended figures, which are not necessarily drawn to scale.

DETAILED DESCRIPTION

Figure 1:
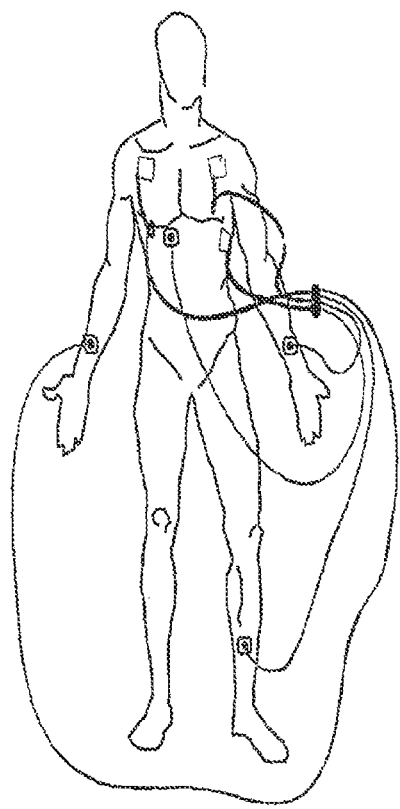
FIG. 1 illustrates the use of a wired monitoring system on a patient.

In the following detailed description, numerous specific details are set forth in order to provide a thorough understanding of the disclosed techniques. However, it will be understood by those skilled in the art that the present embodiments may be practiced without these specific details. In other instances, well-known methods, procedures, components and circuits have not been described in detail so as not to obscure the present disclosure.

Although embodiments are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, a communication system or subsystem, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

Although embodiments are not limited in this regard, the terms "plurality" and "a plurality" as used herein may include, for example, "multiple" or "two or more". The terms "plurality" or "a plurality" may be used throughout the specification to describe two or more components, devices, elements, units, parameters, circuits, or the like.

Before undertaking the description of embodiments below, it may be advantageous to set forth definitions of certain words and phrases used throughout this document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, interconnected with, contain, be contained within, connect to or with, couple to or with, be communicable with, cooperate with, interleave, juxtapose, be proximate to, be bound to or with, have, or the like; and the term "controller" means any device, system or part thereof that controls at least one operation, such a device may be implemented in hardware, circuitry, firmware or software, or combination of at least two of the same. It should be noted that the functionality associated with any particular controller may be centralized or distributed, whether locally or remotely. Definitions for certain words and phrases are provided throughout this document and those of ordinary skill in the art should understand that in many, if not most instances, such definitions apply to prior, as well as future uses of such defined words and phrases.

The exemplary embodiments will be described in relation to communications systems, as well as protocols, techniques, means and methods for performing communications, such as in an epidermal communication network, or in general in any communications network operating using any communications protocol(s) including the body area network. It should be appreciated however that in general, the systems, methods and techniques disclosed herein will work equally well for other types of communications environments, networks and/or protocols.

For purposes of explanation, numerous details are set forth in order to provide a thorough understanding of the present techniques. It should be appreciated however that the present disclosure may be practiced in a variety of ways beyond the specific details set forth herein. Furthermore, while the exemplary embodiments illustrated herein show various components of the system collocated, it is to be appreciated that the various components of the system can be located at distant portions of a distributed network, such as a communications network, node, and/or the Internet, or within a dedicated secured, unsecured, and/or encrypted system and/or within a network operation or management device that is located inside or outside the network. As an example, a wireless device can also be used to refer to any device, system or module that manages and/or configures or communicates with any one or more aspects of the network or communications environment and/or transceiver(s) and/ or stations and/or access point(s) described herein.

Thus, it should be appreciated that the components of the system can be combined into one or more devices, or split between devices, such as a transceiver, an access point, a station, a network operation or management device, a node or collocated on a particular node of a distributed network, such as a communications network and can be docketed onto a system on a chip, system on a module and the like for communicating over the body network. As will be appreciated from the following description, and for reasons of computational efficiency, the components of the system can be arranged at any location within a user and/or network without affecting the operation thereof.

Furthermore, it should be appreciated that the various links, including the communications channel(s) connecting the elements can be wired or wireless links or any combination thereof, or any other known or later developed element(s) capable of supplying and/or communicating data to and from the connected elements. The term module as used herein can refer to any known or later developed hardware, circuitry, software, firmware, or combination thereof, that is capable of performing the functionality associated with that element. The terms determine, calculate, and compute and variations thereof, as used herein are used interchangeably and include any type of methodology, process, technique, mathematical operational or protocol.

Moreover, while some of the exemplary embodiments described herein are directed toward a transmitter portion of a transceiver performing certain functions, this disclosure is intended to include corresponding and complementary receiver-side functionality in both the same transceiver and/or another transceiver(s), and vice versa.

Embodiments provide novel networking mechanisms that facilitate patient monitoring while using a wireless monitoring device. A means for communicating with the wireless monitoring device can include an ECN and/or other body area networks and can be adapted to communicate with the ECN and other external devices via an ECN enabled module. The use of the ECN can provide efficient communication using analog processing for low power, low frequency and low computational costs. Other advantages exist as well as will be discussed herein.

The invention describes herein relates to a wireless ECG. The invention solution presents a safe, intuitive means for making ECG measurements without the use of wires. It provides an ECG measurement system with a higher degree of comfort and easier management for the practitioner. Further, the invention introduces a two charging schemes that are intrinsically safe and reliable. Still furthermore, the invention describes a way of synchronizing the sensors on the monitoring device by way of a master/slave synchronization method in order to provide reliable measurements. Having described the invention, alternatives and embodiments may occur to one of skill in the art.

FIG. 1 illustrates the use of a wired monitoring system 100 on a patient. As illustrated in FIG. 1, the perspective view of the wired monitoring system 100 can include the use of an ECG monitor device with wired leads. FIG. 1 is incorporated herein in its entirety from U.S. Pub. Appl. No. 2010/0234746 to Frederick Sebelius. Figure illustrates, for example, how the wired monitoring system can be connected to a user. As apparent from FIG. 1, a wired monitoring system can be quiet cumbersome to operate. For example, the wires can be tugged, disconnected and set off lead-off alarms, the lead connections can be incorrectly situated leading to an incorrect reading, or the connections can be exposed to RF interference. Even further, a user has an increased probability of infection due to bodily fluid exposure by the wires.

Figure 2A:
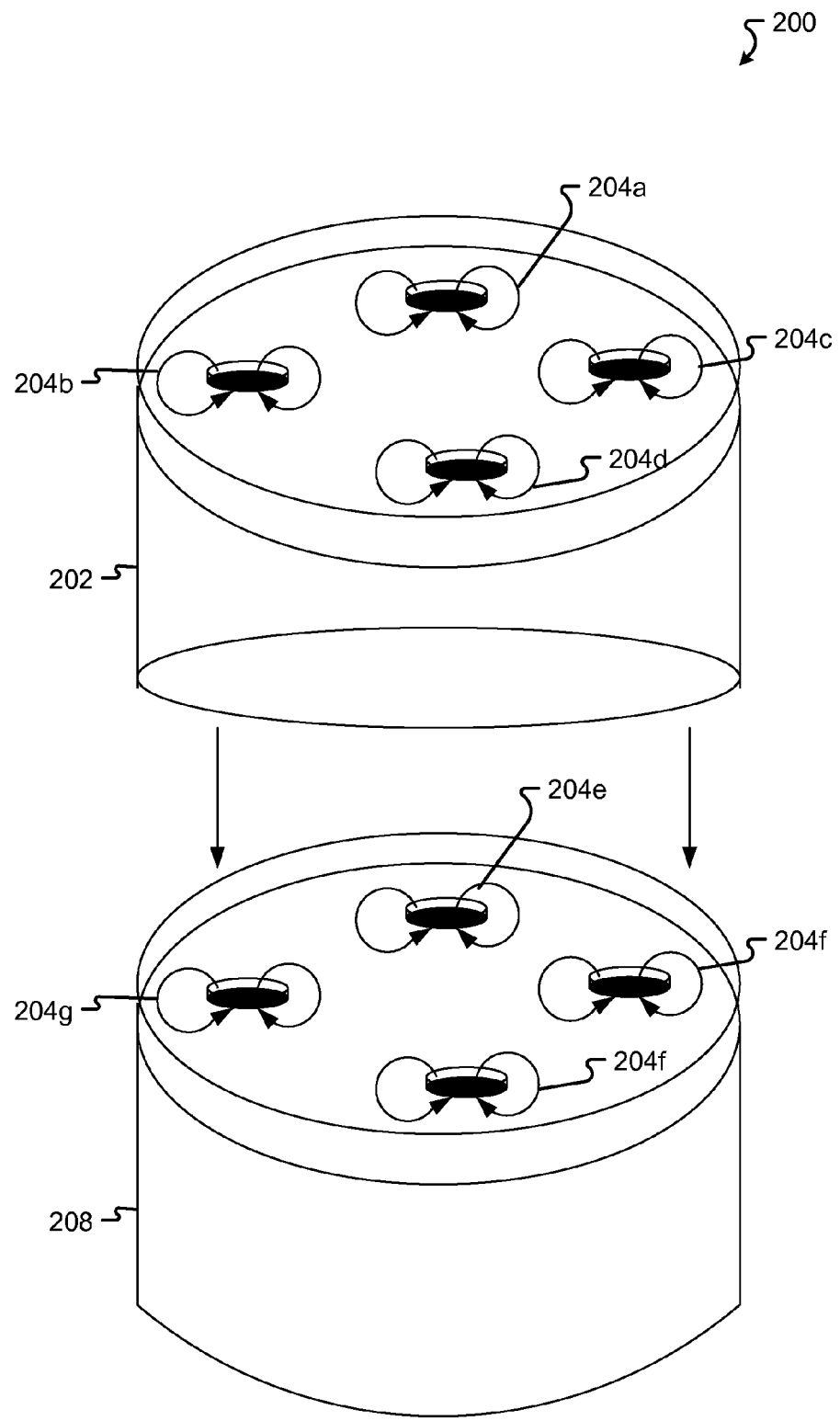
FIG. 2A illustrates a DC mode charging configuration.
Figure 2B:
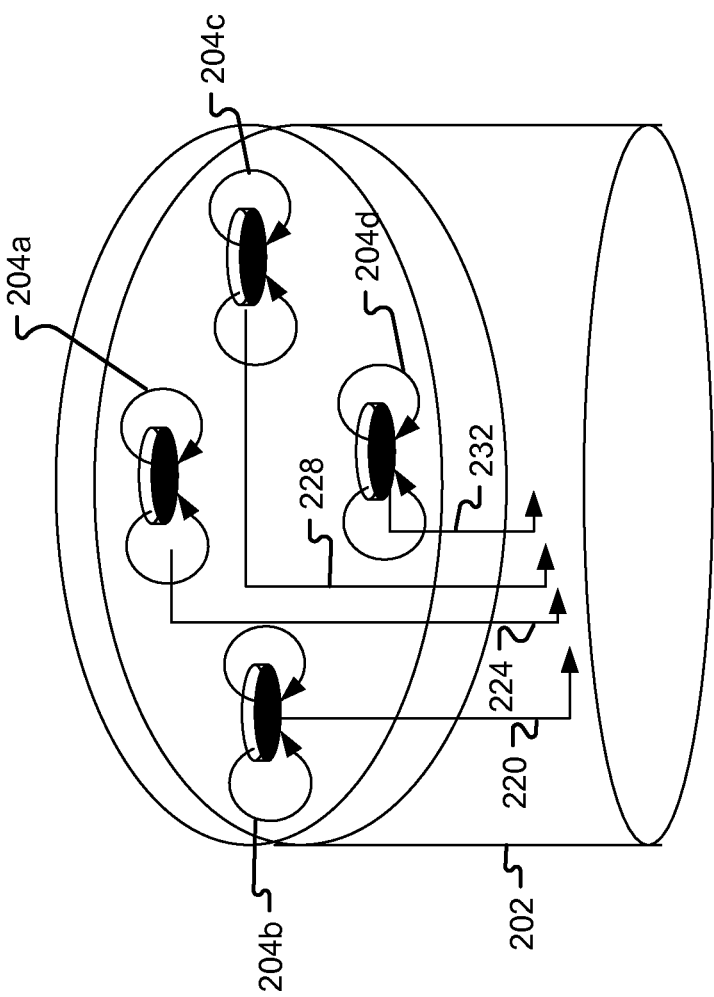
FIG. 2B illustrates a DC mode charging configuration.

A wireless monitoring device can overcome these deficiencies. For example, a user can be provided with a simple yet intuitive device that adheres to the user to enable a less cumbersome means for monitoring. The device can be a wireless ECG monitor, for example, that provides access to data logs, monitors the user, and even includes a safe intrinsic method for charging. The charging can occur via a device enclosure as illustrated in FIGS. 2A and 2B. FIGS. 2A and 2B illustrate DC mode configurations. FIG. 2A displays a perspective view of a device enclosure 200 configured for DC charging. The device enclosure 200 includes a top charging sleeve 202 and a bottom docking sleeve 208. For intrinsic safety and for proper alignment, the enclosures top and bottom sleeves 202,208 can include magnetic polarities that provide an asymmetrical configuration for safe charging. The magnetic polarities can include anodes and cathodes 204a-204g. In one example, 204a and 204e can be the cathodes, while 204b-d and 204f-g are anodes. The top charging sleeve 202 can be equipped with matching counterparts that are identically asymmetrical to the bottom docking sleeve 208. By creating a monitoring device with magnetic polarities, a limited number of permutations fits are available, this provides a guide for correct docking of the charging device enclosure 200. The strong magnetic force exerted by the anodes and cathodes, 204a-204g, ensures a strong interaction between the top charging sleeve 202 and the bottom docking sleeve 208, which can be easily attached and/or removed. In addition, by providing this symmetric configuration, the enclosure between the bottom docking sleeve 208 and the top charging sleeve ensure that the magnetic fields will not impact the integrity of the signal. In another example, 204a and 204e can be anodes, and 204b-d and 204f-g are cathodes. The configuration of the anodes and cathodes, 204a-204g can be arranged in any configuration such that a symmetric configuration is achieved for safe intrinsic charging. Alternatively, the anodes and cathodes, 204a-204g can be arranged in an asymmetric configuration.

In addition, the battery and charging circuitry can be embedded within the charging sleeve 202. FIG. 2B shows a perspective view of the charging implementation. In FIG. 2B, the top charging sleeve 202 is presented with at least one configuration of the circuitry. The anodes and cathodes 204a-204d can be configured to connect to clocks, buses and other system protocols. In one example, anodes and cathodes 204a and 204d can be assigned to the SMCLK 224 and SMDATA 232 clock roles, respectively from the System Management Bus Protocol and anodes and cathodes 204b and 204c can be assigned to $V^+$ 220 and/or $V^-$ 288. The incorporation of communication protocols between charger and module (and interoperability with other common protocols such as I2C) allows for simple integration with a host processor. Components, including, but not limited to LEDs, piezos, GUIs, etc., can be used to indicate charging. The magnetic components can be conductive metals including, but not limited to gold, silver, aluminum, zinc, nickel, brass, bronze, iron, platinum, steel, lead, etc., and can be non-corrosive.

Smart detection technology can be incorporated into the monitoring device to ensure effective charging and in instances where most appropriate for the user. For example, the device can be activated for charging when attached, and verified by a hand-shake between the charger and a host system. The communication between the charger and host system can occur through a bus and only if charging unit is properly detected.

Figure 3:
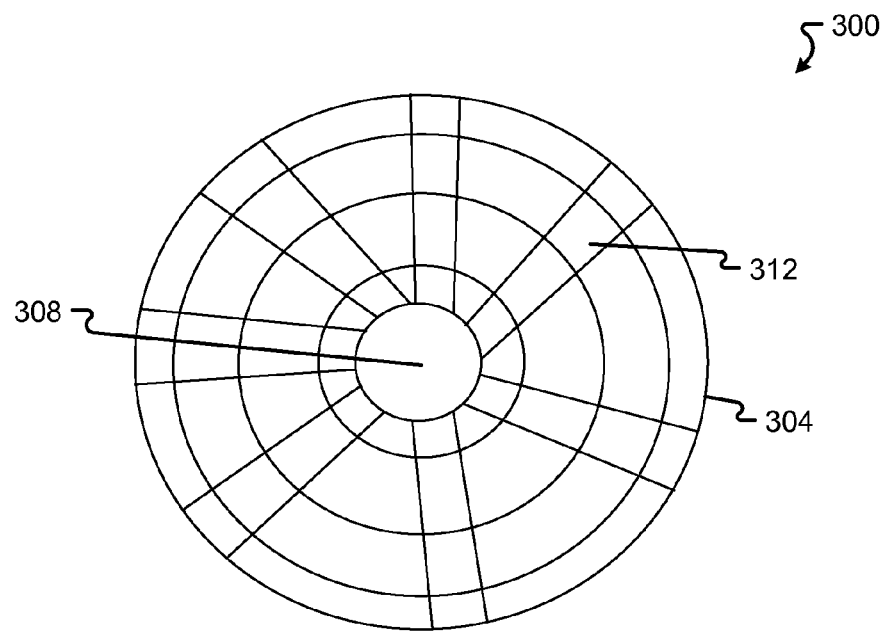
FIG. 3 illustrates a device with scroll wheel.

The monitoring device can therefore present multi-user interface functions and locking mechanisms. For example, the monitoring device 300 can include a scroll wheel 304, as illustrated on FIG. 3. The scroll can provide a safe means for locking the device, avoiding accidental triggers. The scroll wheel 304 can further be used to retrieve a user's information by means of the scroll wheel 304. The magnetic contacts, as described above and in conjunction with FIG. 2, can preferably serve as a multi-input capacitive touch user-interface and even more preferably the magnetic contacts are positioned at various locations as the wheel is adjusted, providing for varying services including but not limited to patient's records, ECG data and other menu items. The scroll wheel 304 can for example, work similar to that of a pattern-lock on a smartphone. That is to say, the scroll wheel 304 can rotate in a series of directions (i.e. 2 turns clockwise, 1 counterclockwise) to enable user input. In many embodiments of the present invention, the number of contacts vary, increasing the number of patters that may be added. In one embodiment, the user input screen may be configured to time-out after non-use for a predetermined number of minutes. In another embodiment, a ½ turn in the clockwise direction can retrieve user data. In another embodiment, rotation in the counter-clockwise direction can retrieve or permit one or more functions. The number of rotations, combination of rotations and direction of rotation is not limited and can include one or more configurations. In addition to the scroll wheel 304, the monitoring device 300 on FIG. 3, can also include capacitive touch inputs 312 and organic light emitting diode (OLED) 308 for user interaction. Alternatively or additionally, the monitoring device 300 can include an LCD (not shown) screen for at least user interaction, data retrieval, and user monitoring. The capacitive touch device can be directed to the use of the interactive scheme in which the monitoring device may be wirelessly controlled by a peripheral communication device. Such communication device may include but not limited to a laptop, tablet, smartphone, etc. Such external connectivity provides further control and customization the device. Therefore, the user can now have access to dynamic switching, zooming and programming (i.e. entering user data, network info, selecting menu options, etc.)

Figure 4:
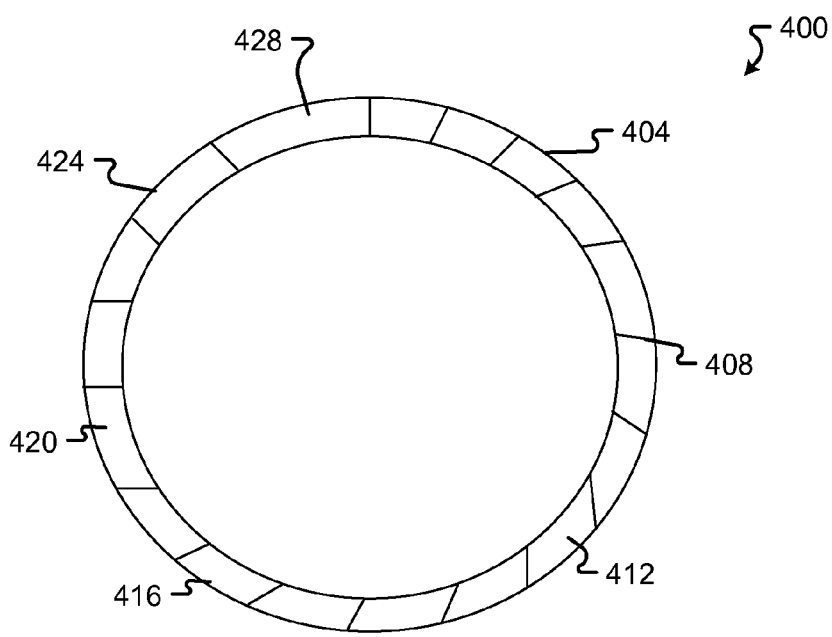
FIG. 4 illustrates the perimeter of the adhesive patch of a monitoring device.

FIG. 4 illustrates the perimeter of the adhesive patch of a monitoring device. FIG. 4 further provides a schematic that is an exemplary extension to the device configuration used in FIGS. 2A-2B, wherein four contacts 212 where used. The arrangement of the contacts, are not limited to 4 and/or placement of the contacts can be arranged in a circular, triangular, rectangular, polygonal, mesh, hexagonal, star, diamond or any other arrangement including preferably in a parallel manner. The number of contacts may be any number greater than two. For example, n conductive elements may be arranged around the circumference of the device as illustrated in FIG. 4.

In this embodiment, the monitoring device 400 can be configured n-pairs of electrodes 304 organized concentrically around the perimeter of the adhesive patch. The placement creates a thin film, flexible electrode angular array. This arrangement allows selection of any pair of electrodes 404 at any given time. The electrodes can be used for example, but not limited to capacitive charging 412, in conjunction with a system management bus protocol 416, for general ECG measurement 420, as a multi-input capacitive user-interface 424, and for communication with an ECN enabled module 428. In addition, this configuration provides simplicity and is useful as ultra-low power. The thin film array placement can be plated directly onto a PCB board and/or the spacing between consists of an insulator block 324.

Figure 5A:
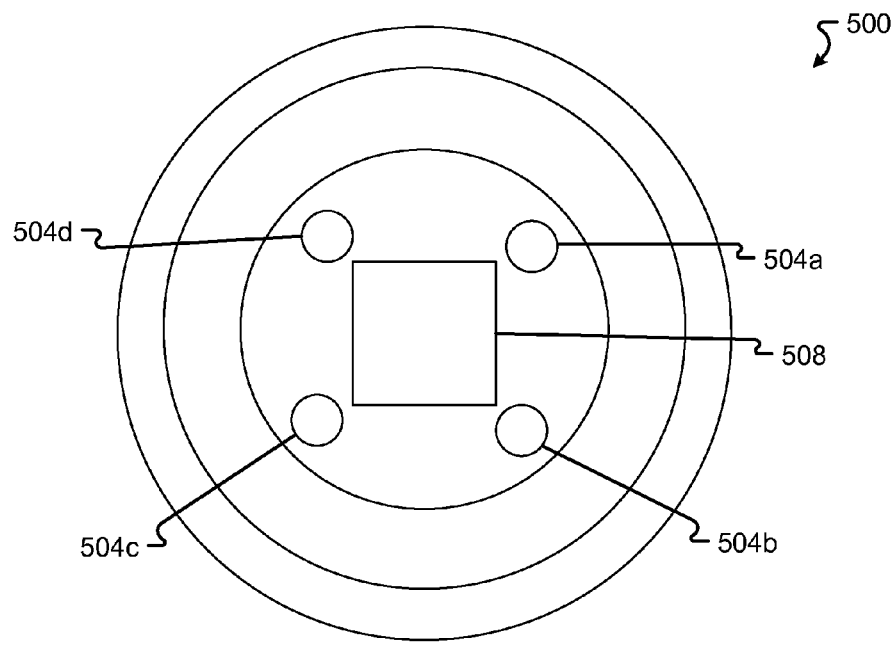
FIG. 5A illustrates a perspective view of a monitoring device.
Figure 5B:
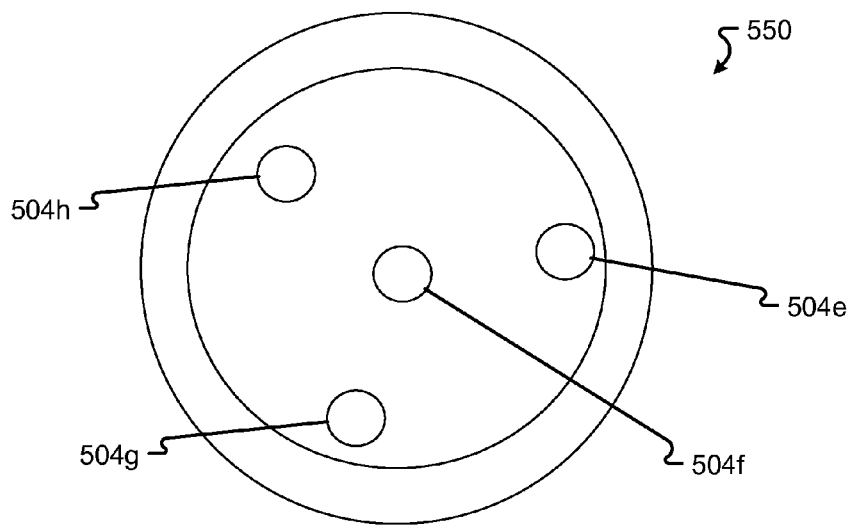
FIG. 5B illustrates a secondary perspective view of a monitoring device.

FIGS. 5A-5B illustrate perspective views of the monitoring device 500, 550. Although only examples of a possible design, FIGS. 5A and 5B provide varying view. FIG. 5A illustrates the front-side view 500 of the device with four contacts 504a-d, and at least an LCD 508 and/or OLED (not shown). FIG. 5B illustrates the back-side view 550 of the monitoring device. The magnetic contacts 504a-504g can be gold plated for efficient charge transfer and to prevent possible corrosion caused by environmental factors.

Figure 6:
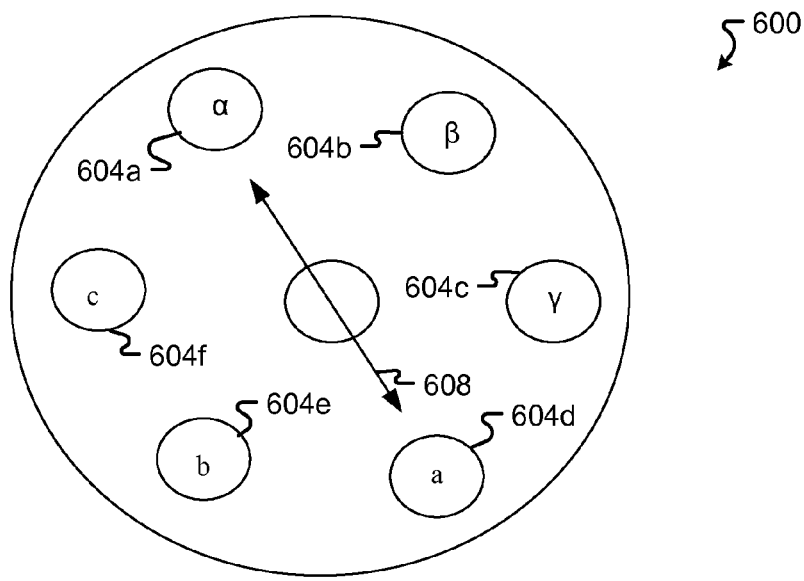
FIG. 6 illustrates an electrode design for a monitoring device.

FIG. 6 illustrates a contacts design for a monitoring device. FIG. 6 further illustrates that contacts/electrodes 604a-604f can be designed to provide greater signal amplitude by increasing the space between the diametrically opposed pairs of contacts/electrodes 604a-604f. As the distance 608 between the contacts increases, the greater the signal. In one example, the distance between contacts 604a and 604d is increased. In another example, the distance between contacts 604b and 604 e is increased. Still in another example, the distance between contacts 604c and 604d is increase. The distances 608 between the contacts can be increased between any two or more contacts. The distance 608 between two contacts can be different than the distance between any other two contacts. The distance between two or more contacts can be the same. The distance between any two contacts can be different for each contact.

Figure 7:
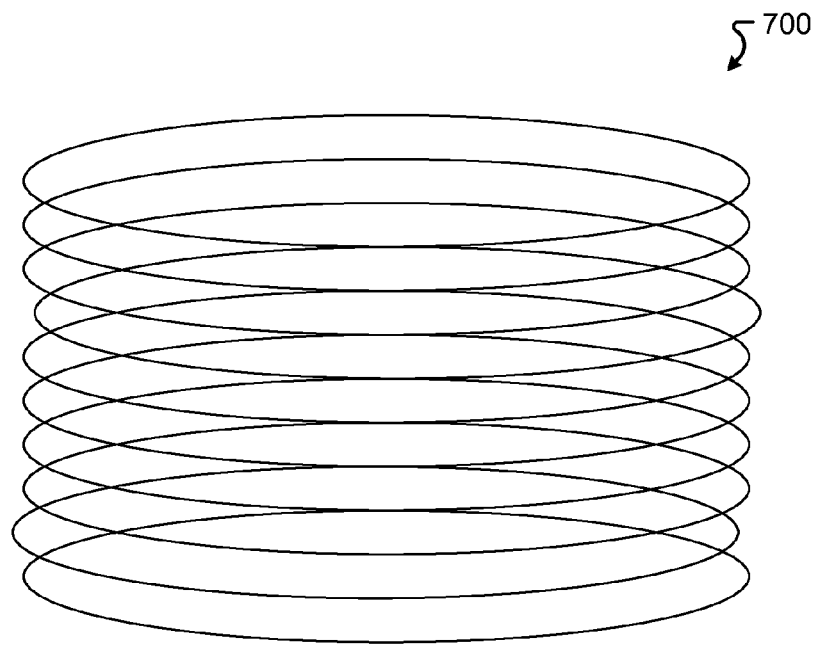
FIG. 7 illustrates a transmit coil for inductive coupling.

In addition, to the use of the four contacts for charging as described above and in conjunction with FIGS. 2A and 2B, FIG. 7 illustrates a transmit coil 700 for inductive charging. By using a magnetic ring/transmit coil 700 along both the perimeter of both the top and bottom of the monitoring device with the multiple contacts, secure coupling can achieved. In one example, the top side of the monitoring device can be disposable. In another example, the bottom side of the monitoring device is disposable. Still in another example, the disposable side can be employed by magnets. Still yet in another example, coupling can be achieved using a material with a highly magnetic permeability such as, but not limited to an un-magnetized iron. The transmit coil 700 can be slipped over the device enclosure (i.e. top charging sleeve and/or the bottom docking sleeve) integrated into the monitoring device. In one example, the magnetic contacts (i.e. cathodes and anodes) can still be present, however charging does not take place across them. In another example, the magnetic contacts are present and charging occurs across the magnetic contacts and on the transmit coil 700. The use of transmit coil 700 can produce an alternating current which can be passed through the top charging sleeve. The current can be inductively coupled onto a second coil/receive coil (similar to transmit coil 700) where it can be rectified and conditioned to charge a smaller capacity on-board battery. Modulation can be applied to the inductive coupling to the inductive charging current to transmit information between the monitoring device and the charging unit.

Figure 8:
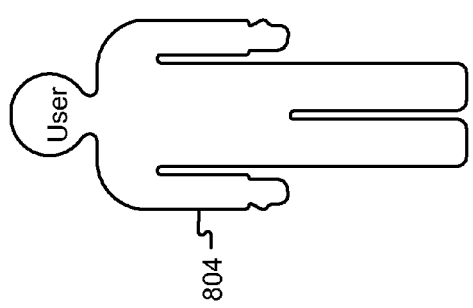
FIG. 8 illustrates an exemplary human body of capacitance
Figure 8:
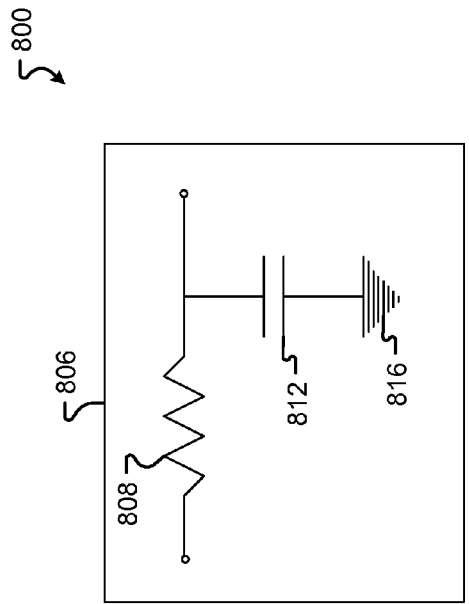

Information can also occur between the monitoring device and other devices located on the body and/or external to the body. For example, the monitoring device can communicate with a wearable device, such as a band, clock, glasses, etc. In one example, the communication can occur on the body, via the use of an epidermal communication network (ECN). Communication can occur over an epidermal communication network because the human body can be modeled as an RC network. FIG. 8 illustrates an exemplary model of a Human Body Model of Capacitance 800. Since body resistance and capacitance are both physical properties of the human body, the human body/user 804 can be modeled as a simple RC low-pass filter network 806. The RC low-pass filter 806 illustrated in FIG. 8 can include a resistor 808 and a capacitor 812 connected in series and a ground 816. The input point 820 and/or output point 824 can be an output point anywhere on the epidermis of a user 804. A voltage can be transmitted from the user 804 to point 824, where point 824 outputs a proportional, attenuated voltage to that applied at point the input of the user 804.

Figure 9:
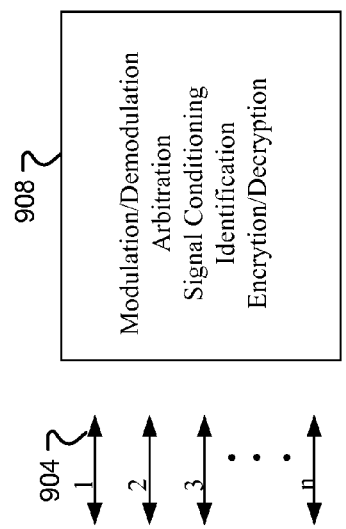
FIG. 9 illustrates a communication system using an epidermal bus.
Figure 9:
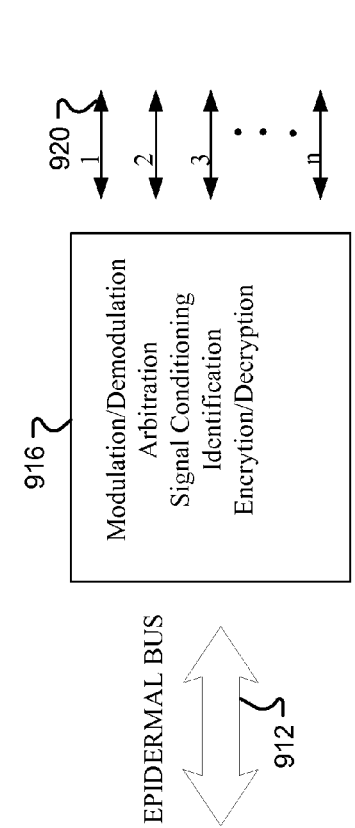

FIG. 9 illustrates a communication system using an epidermal bus. That is, the communication system of FIG. 9 illustrates the use of the human body as an epidermal bus 912 for communication between two devices. The data can be transmitted and/or received at ECN transceivers 908, 916 via the epidermal bus 912 and/or from standard data buses 904 and 920. The ECN transceivers 908, 916 can be any type of communication device including wearable devices such as but not limited to ECG monitors, watches, bracelets, necklaces, bands, body bands, glasses, jewelry, fabric, cellular phones, smart phones, iPads, smart pads, laptops, PDAs, etc. The ECN transceivers, can further include communication devices that are ECN enabled to provide wireless communication between each other, between wired devices, between external devices (i.e., Bluetooth®, NFC, WiDi, WLAN communications, etc.) and any other type of communication system. The ECN transceivers 908 and 916 if not ECN enabled, can include an ECN interface to transfer, upload, and/or download information between devices with the epidermal bus 912. The ECN transceivers 908 and 916 can further include all the major components for signal processing including modulation/demodulation, arbitration, signal conditioning, identification and encryption/decryption. Further details regarding the basic components in the ECN transceiver 908, 916 will be discussed below and in conjunction with FIG. 10 and FIG. 12.

Figure 10:
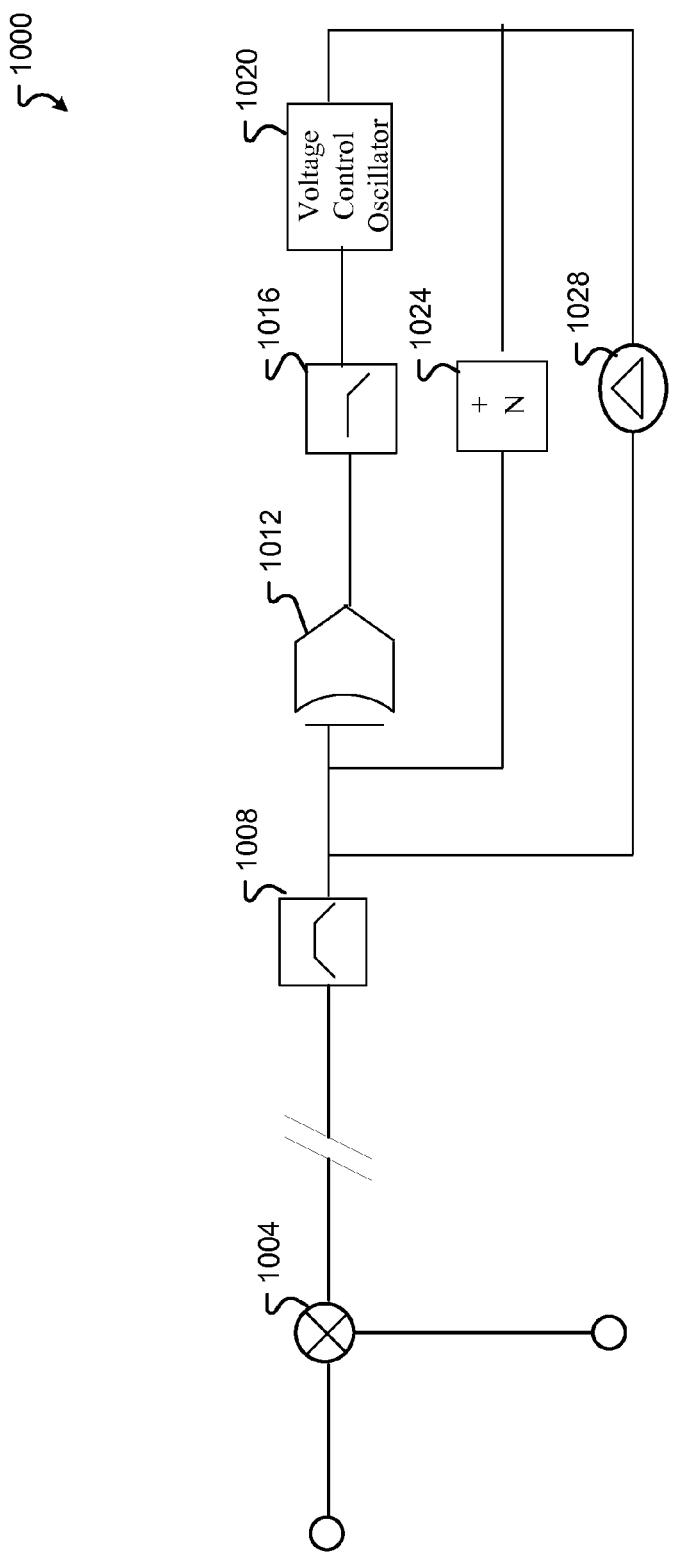
FIG. 10 illustrates a modulation/demodulation system.

FIG. 10 illustrates a basic modulation/demodulation system 1000. The modulations/demodulation system 1000 from FIG. 10 provides exemplary components used in conjunction with the modulation process used in ECN communications. The basic modulation/demodulation system 1000 can include mixers 1004, filters 1008, 1016, phase comparators 1012, oscillators 1020, samplers 1024, summers 1028, etc. The filters can include tunable band pass filters, low pass filters, notch filters, digital filters, IIRs, FIRs, passive filters, active filters, analog filters, digital filters, etc. The modulation/demodulation scheme for use with communications over the ECN network can include On-Off Keying modulation. On-Off Modulation is a simple form of Amplitude-Shift Keying modulation which provides for a more spectral efficient modulation than FSK modulation. Other modulation/demodulation schemes can be used for communication over an ECN network as well. For example, the modulation schemes can include Amplitude Modulation, Frequency Modulation, Phase Modulation, Quadrature Amplitude Modulation, Space Modulation, Single-Sideband Modulation, Amplitude Shift Keying, Frequency Shift Keying (FSK), Phase Shift Keying (PSK), Quadrature Phase Shift Keying (QPSK), Spread Spectrum, Orthogonal Frequency-Division Multiplexing (OFDM), OFDMA, etc.

Figure 11:
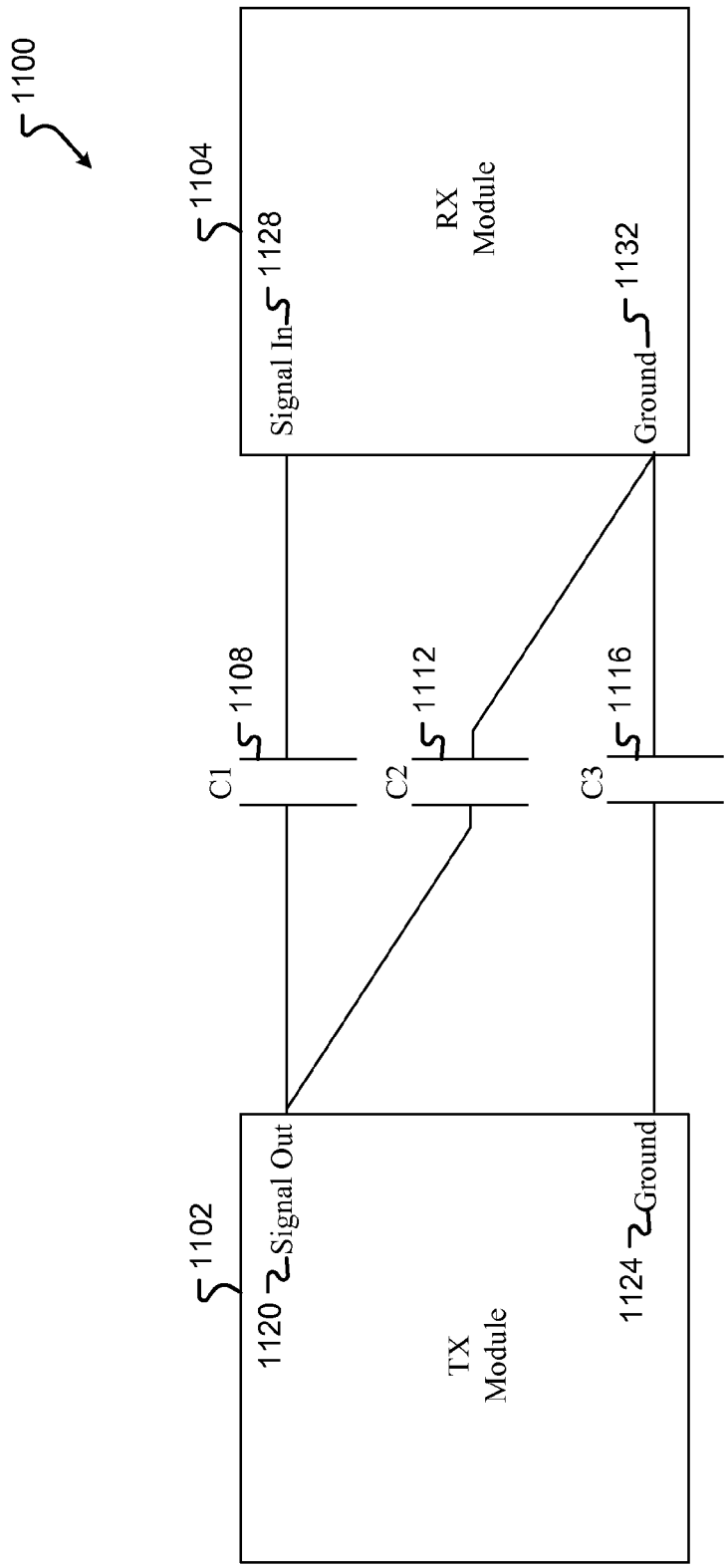
FIG. 11 illustrates coupling as it occurs on the ECN.

For the communication to occur over the ECN network, coupling as illustrated in coupling diagram 1100 on FIG. 11 occurs. Coupling is the transfer of energy within a network by means a capacitance between two nodes and is often known as capacitive coupling. In some instances stray or parasitic coupling occurs in which unavoidable capacitance or energy transfer occurs due to the proximity of components. FIG. 11 illustrates the coupling diagram where a transmitter module 1102 and a receiver module 1104 are communicating over an ECN network. In the communication between the devices, a signal input/output 1120, 1128 and ground 1124, 1132 will at least exist at each transmit and receive module 1102, 1004. In communicating over the ECN, a signal departing from the signal output of the transmit module 1102 can take one of two routes, the signal can couple C2 1112 the receive ground 1132 and/or can couple C1 1108 to the signal in 1128. Alternatively or additionally, the transmit module 1102 can include a ground 1124 which couples C3 1116 to the receiver module 1104 via a ground 1132. In one example, the coupling C2 1112 that occurs between the ground 1124 of the transmit module 1102 and the ground 1132 of the receive module 1104 occurs through air. In addition, the coupling C1 1108 between the signal out 1120 and the signal in 1128 occurs through the skin of a user. Therefore, coupling C2 1112 takes the form of parasitic coupling. When this occurs, the path of the coupling C1 1108 is stronger that of the coupling C2 1112 and the signal is transmitted over the ECN network. Thus, the dielectric properties of the human body or a user create a better capacitor for coupling C1 1108 than free air without the need for an earth ground at a low voltage.

$$C_{body} > C_{air}$$

In some instances, to increase the coupling between the signal out 1120 and the signal in 1128, i.e., to increase coupling C1 1109, bandages, lotions, lubricants, etc., can be added. For example, an adhesive patch can include microspikes which aid in the coupling and signal transfer between the monitoring device and/or another wearable device, a wired device, a wireless device and other devices of the like. The microspikes can include an adhesive bandage, patch other similar material on the monitoring device or on as a separate mechanism that includes miniature speared objects that can minimally penetrate the skin to a more conductive layer for better user coupling and signal transmission. Alternatively or in addition, a body lotion, lubricant, or other viscous substance can be applied on the epidermis of the user to increase the conductivity for better signal transmission.

In another example, galvanic coupling can occur between the transmit module 1102 and the receive module 1104 which enables body network communications or the communication over an epidermal communication network (ECN). In galvanic coupling, the signal will travel and energy will transfer between nodes (i.e. ground 1132, signal in 1128, etc.) and across various parts of the human body/user, with coupling occurring at the signal in 1128 where the wearable device or monitoring device may be. In yet another example, earth ground coupling occurs and the signal is transferred through the epidermis. The use of galvanic coupling for intra-body communications further described in "An Efficient Pulse Position Modulation Transmitter for Galvanic Intrabody Communications" to MirJojjat Seyedi and is incorporated herein in its entirety. Personal area networks (PAN) are used in the signal transmission and explained through galvanic coupling. PAN is explained in further detail in both "Personal Area Networks (PAN): Near-field intra-body communications." M.S. thesis to T. G. Zimmerman, and U.S. Pat. No. 5,914,701 to Gersheneld et. al. and are incorporated herein in their entirety. Additional coupling details are also found in "Body-Coupled Communications—Experimental characterization, channel modeling and physical layer design," M.S. thesis to N. S. Mazloum and is incorporated herein in its entirety. Furthermore, in some instances where galvanic coupling is used through body data transfer occurs. In other instances, where parasitic coupling is used, through body data transfer also occurs. U.S. Publication No. 2013/0142363, "Devices and Methods for Transferring Data Through A Human Body" to B. Amento details a method for transferring data to a device though a user and is incorporated herein in its entirety. Still further, in some instances, implantable Intra-Body communication can be used in conjunction with galvanic coupling. As appreciated in view of the guidance provided herein, including a more detailed description as described "Development and Prospect of Implantable Intra-Body Communication Technology" by S. Zhang, is further incorporated by reference herein, various combinations of intra-body communication is within the scope of the present invention.

Figure 12:
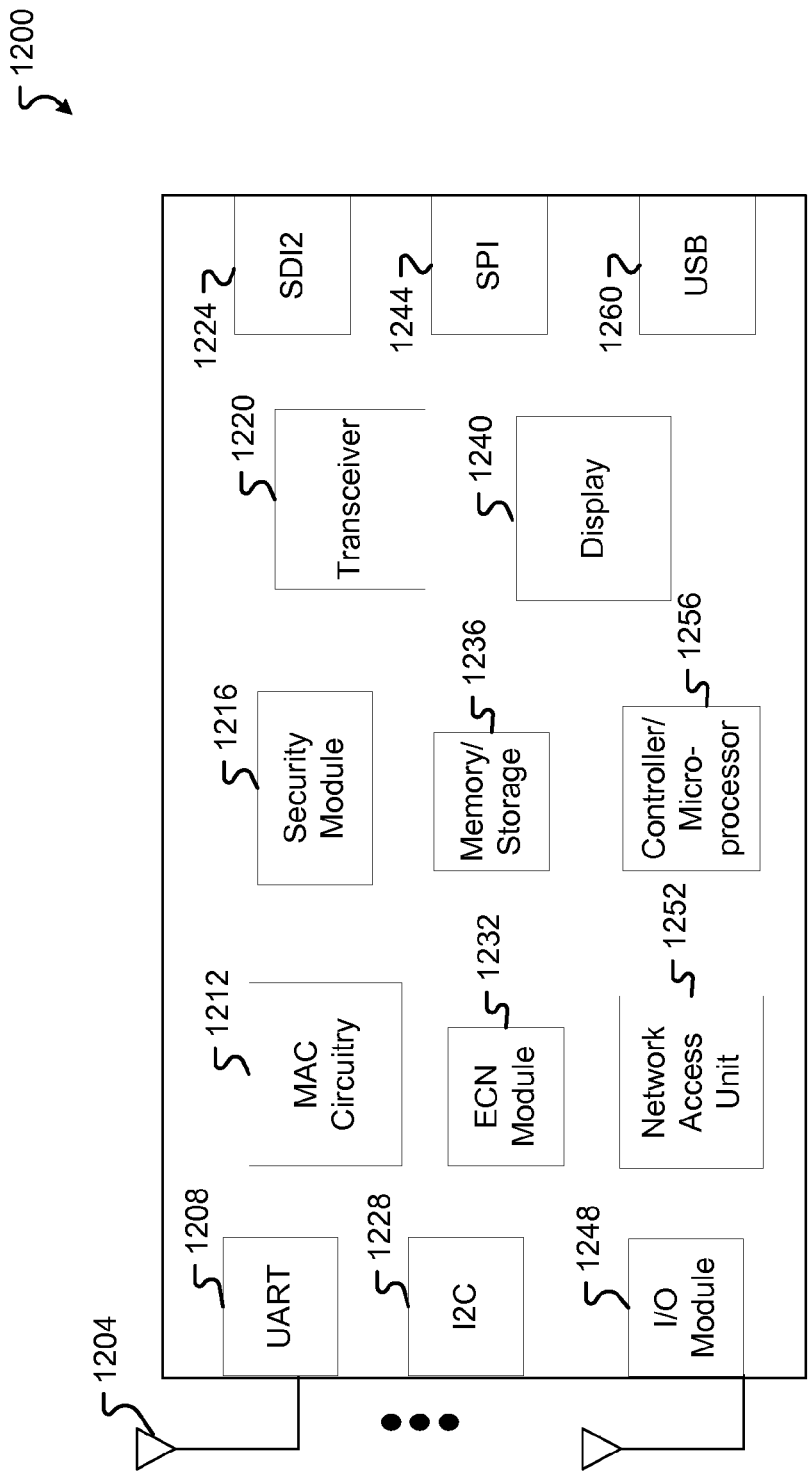
FIG. 12 illustrates an ECN enabled module.

FIG. 12 illustrates an ECN enabled module 1200. The ECN enable module 1200 is a module that can work as an interface for ECN communications in instances or in conjunction to wearable and/or non-wearable devices that are ECN enabled. The ECN enabled module 1200 is a module that can be used to docket or connect a wearable device, wired, or wireless device for communication. The ECN enabled module 1200 can work as a System on a Module (SOM). Alternatively, the ECN enabled module 1200 can be a stand-alone module that can reside on the same chip as a system on a chip (SOC). In addition, the ECN enable module 1200 can further include wearable electrode chips, stand-alone chips, and other chips on modules which enable access to ECN. External systems to connect to can include master/slave modules, modules whose internal operation is abstracted and/or other such system which can be docketed onto an ECN interface such as the ECN enable module 1200, for signal transmission using the ECN.

The architecture of the ECN enabled module can closely resemble a communication device with various output ports (i.e., 1208, 1228, 1248, 1224, 1244, 1260) for docking and/or connectivity with other components. As a System on a Module (SOM), the ECN enable module 1200 can include one or more antennae 1204 for signal transmission and reception. The antennae can provide for Single-Input Single-Output (SISO) communications, Single-Input Multi-Output (SIMO) communications, Multi-Input Single-Output (MISO) and Multi-Input Multi-Output (MIMO) communications. Additionally or alternatively, the antennae can be used in Bluetooth®, NFC, IR, etc., communications. The antennae can include, but are not limited to dipoles, microstrip, monopoles, slot, bow-tie, folded, loop, yagi-ura antennae.

The ECN enabled module 1200 can also include a network access unit 1252 and MAC Circuitry 1212 for signal transmission and contention. A transceiver 1220 is included in the ECN enabled module 1200 for signal processing. In some instances, the signal processing can occur before the ADC for lower consumption and signal transmission at a lower frequency and savings in clock cycles (i.e. the front-end is analog). Power consumption can be minimized through the processing of the signal in the analog domain enabling processing without the need for costly clock cycles and processing in the digital domain. The signal processing both analog and/or digital can occur in the controller/microprocessor 1256. The transceiver can operate at frequencies as low as 500 KHz which can include ping frequencies at +/−10 KHz (i.e., 510 KHz and 490 KHz). Further details regarding the transceiver (i.e. or independently transmit and receive modules) are described above and in conjunction with FIGS. 8 and 9.

Processing, data retrieval and/or data storage, Memory/Storage module 1236 can be included in the architecture of the ECN enabled module 1200. The Memory/Storage 1236 module can include but is not limited to SDRAM, ROM, RAM, memory arrays, and NVRAM. The Memory/Storage module 1236 can work in conjunction with an ECN module 1232, which can work as an application for allowing the connectivity between the various communication devices and the ECN. The ECN module 1232 can further include instructions for allowing signal transmission and processing. Further, the ECN module 1232 can include rules and lookup tables for correct device matching and configuration.

For secure transmission between the wearable devices, wired and wireless devices, a security module 1216 can provide appropriate keys such as, WEP and WAP. Signal encryption can also occur in the security module 1216 and/or controller/micro-processor 1256 and/or transceiver 1220. Like the monitoring device described above, the SOM ECN enabled module 1200 can include a display 1240 for user interaction if applicable. The ECN enabled module 1200 can also include a photoplethysmographic sensor (not shown) for monitoring health/fitness including heart rate logs. In addition, as previously discussed, multiple-interfaces are available for data transmission and reception between the communication devices. The interfaces can include at least a UART 1208, I2C 1228, SDI2 1224, SPI 1244, USB 1260 and others of the like in the I/O module 1248.

Figure 13:
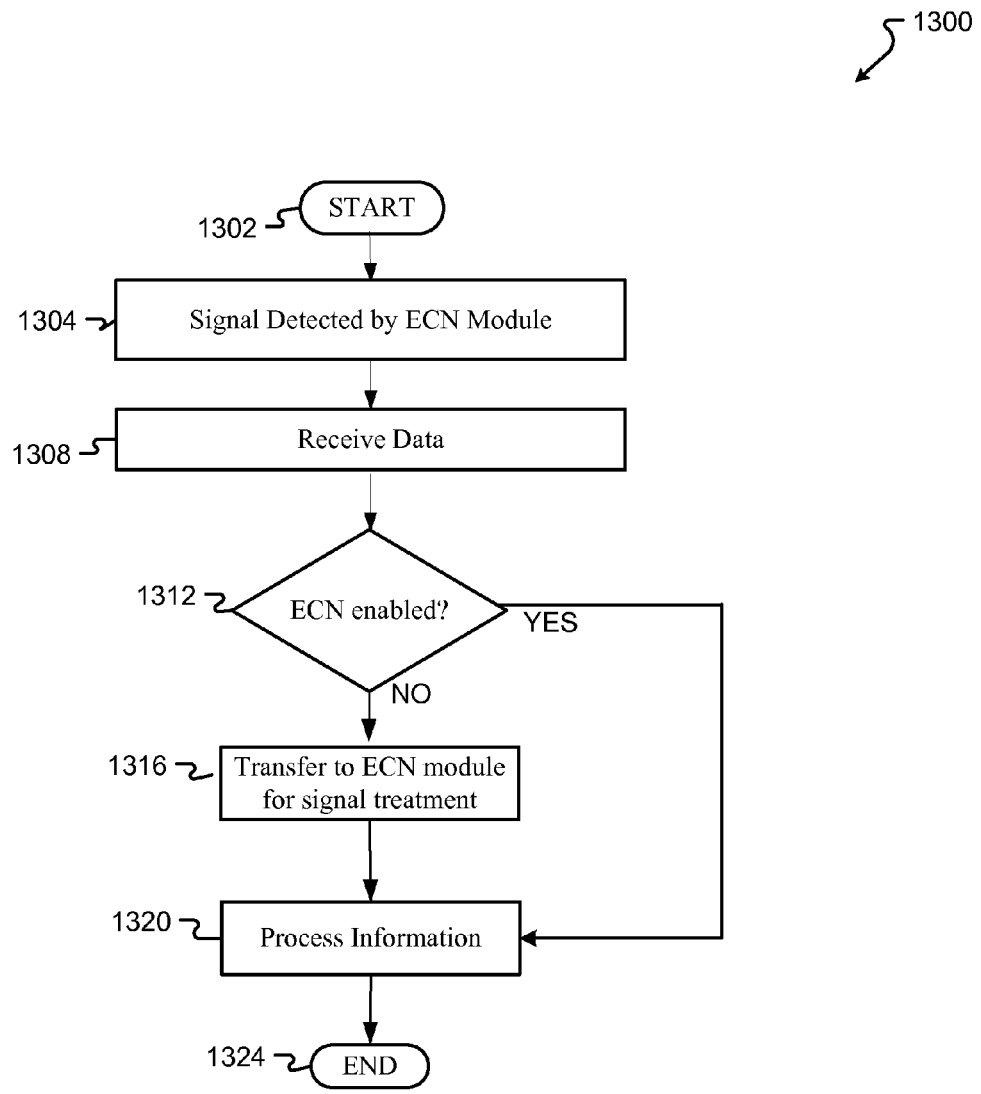
FIG. 13 is a flowchart illustrating ECN communication.

FIG. 13 is a flow chart illustrating exemplary signal detection over an ECN network. In particular, the association begins in step 1302 and continues to step 1304, where signal detection occurs by an ECN enabled module. At this stage, the ECN enabled module will receive the signal at step 1308 and determine if the signal received arrived from a device that was ECN enabled in step 1312. If the signal was transmitted by an ECN enabled device, the device used and ECN interface, or the signal was arrived in its appropriate format, then the signal is transferred for processing at step 1320. Alternatively, if the signal was not in an appropriate format, then the signal can be transferred to an ECN module or application for signal treatment for appropriate processing and transmission over the ECN network. Once the signal is treated at step 1316, the signal is ready for processing at step 1320. After processing, the process ends at step 1324.

The exemplary systems and methods are described in relation to a wireless health monitoring device enabled to operate on an ECN and associated communication hardware, software and communication channels. However, to avoid unnecessarily obscuring the present disclosure, the following description omits well-known structures and devices that may be shown in block diagram form or otherwise summarized.

For purposes of explanation, numerous details are set forth in order to provide a thorough understanding of the present embodiments. It should be appreciated however, that the techniques herein may be practiced in a variety of ways beyond the specific details set forth herein.

Furthermore, it should be appreciated that the various links, including communications channel(s), connecting the elements (which may be not shown) can be wired or wireless links, or any combination thereof, or any other known or later developed element(s) that is capable of supplying and/or communicating data and/or signals to and from the connected elements and/or epidermal communication networks and/or body area networks. The term module as used herein can refer to any known or later developed hardware, software, firmware, or combination thereof that is capable of performing the functionality associated with that element. The terms determine, calculate and compute, and variations thereof, as used herein are used interchangeably and include any type of methodology, process, mathematical operation or technique.

While the above-described flowcharts have been discussed in relation to a particular sequence of events, it should be appreciated that changes to this sequence can occur without materially effecting the operation of the embodiment(s). Additionally, the exact sequence of events need not occur as set forth in the exemplary embodiments, but rather the steps can be performed by one or the other transceiver in the communication system provided both transceivers are aware of the technique being used for initialization. Additionally, the exemplary techniques illustrated herein are not limited to the specifically illustrated embodiments but can also be utilized with the other exemplary embodiments and each described feature is individually and separately claimable.

The above-described system can be implemented on a wireless telecommunications device(s)/system, such an 802.11 transceiver, or the like. Examples of wireless protocols that can be used with this technology include 802.11a, 802.11b, 802.11g, 802.11n, 802.11ac, 802.11ad, 802.11af, 802.11ah, 802.11ai, 802.11aj, 802.11aq, 802.11ax, 802.11u, WiFi, LTE, LTE Unlicensed, 4G, Bluetooth®, WirelessHD, WiGig, 3GPP, Wireless LAN, WiMAX, PAN.

The term transceiver as used herein can refer to any device that comprises hardware, software, firmware, or combination thereof and is capable of performing any of the methods described herein.

Additionally, the systems, methods and protocols can be implemented on one or more of a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device such as PLD, PLA, FPGA, PAL, a modem, a transmitter/receiver, any comparable means, or the like. In general, any device capable of implementing a state machine that is in turn capable of implementing the methodology illustrated herein can be used to implement the various communication methods, protocols and techniques according to the disclosure provided herein.

Examples of the processors as described herein may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, Broadcom® AirForce BCM4704/BCM4703 wireless networking processors, the AR7100 Wireless Network Processing Unit, other industry-equivalent processors, and may perform computational functions using any known or future-developed standard, instruction set, libraries, and/or architecture.

Furthermore, the disclosed methods may be readily implemented in software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with the embodiments is dependent on the speed and/or efficiency requirements of the system, the particular function, and the particular software or hardware systems or microprocessor or microcomputer systems being utilized. The communication systems, methods and protocols illustrated herein can be readily implemented in hardware and/or software using any known or later developed systems or structures, devices and/or software by those of ordinary skill in the applicable art from the functional description provided herein and with a general basic knowledge of the computer and telecommunications arts.

Moreover, the disclosed methods may be readily implemented in software and/or firmware that can be stored on a storage medium, executed on programmed general-purpose computer with the cooperation of a controller and memory, a special purpose computer, a microprocessor, or the like. In these instances, the systems and methods can be implemented as program embedded on personal computer such as an applet, JAVA® or CGI script, as a resource residing on a server or computer workstation, as a routine embedded in a dedicated communication system or system component, or the like. The system can also be implemented by physically incorporating the system and/or method into a software and/or hardware system, such as the hardware and software systems of a communications transceiver.

It is therefore apparent that there has been provided systems and methods for ECG monitoring, the use of an ECN network, and an ECN enabled module for communication over and interfacing with the ECN. While the embodiments have been described in conjunction with a number of embodiments, it is evident that many alternatives, modifications and variations would be or are apparent to those of ordinary skill in the applicable arts. Accordingly, it is intended to embrace all such alternatives, modifications, equivalents and variations that are within the spirit and scope of this disclosure.

The present disclosure, in various aspects, embodiments, and/or configurations, includes components, methods, processes, systems and/or apparatus substantially as depicted and described herein, including various aspects, embodiments, configurations embodiments, sub-combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

We claim:

1. A system comprising:
a memory; and
a transceiver, the transceiver configured to:
    receive data signals from a communication device;
a processor, the processor configured to:
    determine if the communication device is enabled to operate on an epidermal communication network (ECN);
    treat the data signals received for communication over the ECN; and
    process the data signals using an analog-front-end located in the system; and
a docking component for interfacing the communication device to operate on the ECN, wherein interfacing the communication device on the system includes placement of the communication device on the system via direct attachment and/or via at least one of a UART, USB, and SPI; and
wherein the data signals received travel on the ECN and take the form of a parasitic coupling, wherein a path of the parasitic coupling is between a signal-out and a signal-in and occurs through the skin of a user, and said parasitic coupling is stronger than that of a coupling that occurs through the air between a ground of a transit module and the ground of a receive module.

2. A method comprising:
receiving, by a transceiver, data signals from a communication device in a system;
determining, by a processor, if the communication device is enabled to operate on an epidermal communication network (ECN);
treating, by the processor, the data signals received for communication over the ECN; and
processing, by the processor, data signals using an analog-front-end located in the system;
employing a docking component for interfacing the communication device to operate on the ECN, wherein interfacing of the communication device on the system includes placement of the communication device on the system via direct attachment and/or via at least one of a UART, USB, and SPI, and
receiving the data signals that travel on the ECN in the form of a parasitic coupling, wherein a path of the parasitic coupling is between a signal-out and a signal-in and occurs through the skin of a user, said parasitic coupling being stronger than that of a coupling that occurs through the air between a ground of a transit module and the ground of a receive module.

3. A non-transitory computer readable medium having instructions stored thereon that when executed by at least one processor of a communication device perform a method comprising:
receiving, by a transceiver, data signals from a communication device in a system;
determining, by a processor, if the communication device is enabled to operate on an epidermal communication network (ECN);
treating, by the processor, the data signals received for communication over the ECN; and
processing, by the processor, the data signals using an analog-front-end located in the system;
interfacing the communication device with a docking component to operate on the ECN, wherein interfacing the communication device on the system includes placement of the communication device on the system via direct attachment and/or via at least one of a UART, USB, and SPI, and
wherein the data signals received travel on the ECN and take the form of a parasitic coupling, wherein a path of the parasitic coupling is between a signal-out and a signal-in and occurs through the skin of a user, said parasitic coupling being stronger than that of a coupling that occurs through the air between a ground of a transit module and the ground of a receive module.

* * * * *